(12) United States Patent
Berenson

(10) Patent No.: US 8,996,104 B2
(45) Date of Patent: Mar. 31, 2015

(54) PATCHES AND METHOD FOR THE TRANSDERMAL DELIVERY OF A THERAPEUTICALLY EFFECTIVE AMOUNT OF IRON

(75) Inventor: Ronald J. Berenson, Mercer Island, WA (US)

(73) Assignee: FE3 Medical, Inc., San Jose, CA (US)

( * ) Notice: Subject to any disclaimer, the term of this patent is extended or adjusted under 35 U.S.C. 154(b) by 695 days.

(21) Appl. No.: 12/459,183

(22) Filed: Jun. 25, 2009

(65) Prior Publication Data

US 2010/0130910 A1    May 27, 2010

Related U.S. Application Data

(60) Provisional application No. 61/075,720, filed on Jun. 25, 2008.

(51) Int. Cl.
  *A61N 1/30* (2006.01)
  *A61K 9/00* (2006.01)
  *A61K 9/70* (2006.01)
  (Continued)

(52) U.S. Cl.
  CPC .............. *A61N 1/303* (2013.01); *A61K 9/0009* (2013.01); *A61K 9/0021* (2013.01); *A61K 9/7023* (2013.01); *A61K 31/295* (2013.01);
  (Continued)

(58) Field of Classification Search
  USPC ........ 604/20, 21, 22, 501; 424/646, 647, 648; 514/184, 185, 6, 502, 492
  See application file for complete search history.

(56) References Cited

U.S. PATENT DOCUMENTS

| 3,491,187 A | 1/1970 | Ely |
| 4,325,367 A | 4/1982 | Tapper |

(Continued)

FOREIGN PATENT DOCUMENTS

| EP | 0090425 A1 | 10/1983 |
| WO | WO 98/20869 A2 | 5/1998 |

(Continued)

OTHER PUBLICATIONS

Murthy et al., Irontophoresis: Transdermal Delivery of Iron by Iontophoresis:, J. Pharm. Sci., Aug. 2009, 98(8):2670-2676; and online publication DOI 10.1002/jps.21641.

(Continued)

*Primary Examiner* — Kevin C Sirmons
*Assistant Examiner* — Deanna K Hall
(74) *Attorney, Agent, or Firm* — Alston & Bird LLP

(57) ABSTRACT

Embodiments of the invention provide patches for the transdermal delivery of iron-containing compositions to an individual suffering from an iron deficiency. Many embodiments provide an iontophoretic patch for the transdermal delivery of a therapeutically effective amount of iron. The patch comprises an electrode and a reservoir containing a composition comprising ionic iron for the delivery of the therapeutically effective amount of iron. Various embodiments provide methods of using embodiments of the iontophoretic patch for delivering a therapeutically effective amount of iron to an individual suffering from one more forms of iron deficiency including iron deficiency anemia. Such methods can be used for treating and/or preventing the iron deficiency. The amount of delivered iron can be adjusted depending upon various treatment parameters such as patient weight and type and amount of iron deficiency.

42 Claims, 8 Drawing Sheets

(51) Int. Cl.
*A61K 31/295* (2006.01)
*A61K 33/26* (2006.01)
*A61K 38/18* (2006.01)
*A61N 1/04* (2006.01)

(52) U.S. Cl.
CPC ............ *A61K 33/26* (2013.01); *A61K 38/1816* (2013.01); *A61N 1/0448* (2013.01); *A61N 1/0444* (2013.01)
USPC ........................................... 604/20; 604/501

(56) References Cited

U.S. PATENT DOCUMENTS

| | | | |
|---|---|---|---|
| 4,731,049 A | 3/1988 | Parsi | |
| 4,734,090 A | 3/1988 | Sibalis | |
| 4,863,897 A | 9/1989 | Dede et al. | |
| 4,886,489 A | 12/1989 | Jacobsen et al. | |
| 5,310,404 A | 5/1994 | Gyory et al. | |
| 5,328,453 A | 7/1994 | Sibalis | |
| 5,385,543 A | 1/1995 | Haak et al. | |
| 5,503,632 A | 4/1996 | Haak | |
| 5,543,098 A | 8/1996 | Myers | |
| 5,605,536 A | 2/1997 | Sibalis | |
| 5,634,899 A | 6/1997 | Shapland et al. | |
| 5,693,024 A | 12/1997 | Flower | |
| 5,797,867 A | 8/1998 | Guerrera et al. | |
| 5,928,185 A | 7/1999 | Muller et al. | |
| 5,983,130 A | 11/1999 | Phipps et al. | |
| 6,019,877 A | 2/2000 | Dupelle et al. | |
| 6,064,908 A | 5/2000 | Muller et al. | |
| 6,230,051 B1* | 5/2001 | Cormier et al. | 604/20 |
| 6,256,533 B1* | 7/2001 | Yuzhakov et al. | 604/21 |
| 6,314,317 B1* | 11/2001 | Willis | 604/20 |
| 6,330,471 B1 | 12/2001 | Higo et al. | |
| 6,379,324 B1* | 4/2002 | Gartstein et al. | 604/22 |
| 6,512,950 B2 | 1/2003 | Li et al. | |
| 6,553,255 B1 | 4/2003 | Miller | |
| 6,584,349 B1 | 6/2003 | Sage et al. | |
| 6,689,275 B1 | 2/2004 | Gupta | |
| 6,692,456 B1* | 2/2004 | Eppstein et al. | 604/22 |
| 6,731,965 B2 | 5/2004 | Menon et al. | |
| 6,779,468 B1 | 8/2004 | Gupta | |
| 7,137,975 B2 | 11/2006 | Miller | |
| 7,141,034 B2* | 11/2006 | Eppstein et al. | 604/22 |
| 7,255,881 B2* | 8/2007 | Gillis et al. | 424/618 |
| 7,340,297 B2 | 3/2008 | Tamarkin | |
| 7,375,139 B2 | 5/2008 | Aldred | |
| 7,437,189 B2 | 10/2008 | Matsumura | |
| 7,496,401 B2 | 2/2009 | Bernabei | |
| 7,522,954 B2 | 4/2009 | Tedoldi | |
| 7,548,778 B2 | 6/2009 | Roy | |
| 7,558,625 B2 | 7/2009 | Levin | |
| 7,590,444 B2 | 9/2009 | Tanioka | |
| 7,593,770 B2 | 9/2009 | Lerner | |
| 7,611,481 B2 | 11/2009 | Cleary et al. | |
| 7,816,404 B2 | 10/2010 | McCall, Jr. | |
| 8,190,252 B2 | 5/2012 | Imran | |
| 2002/0099356 A1* | 7/2002 | Unger et al. | 604/501 |
| 2003/0060798 A1 | 3/2003 | Fischer et al. | |
| 2003/0065285 A1 | 4/2003 | Higuchi | |
| 2003/0199808 A1 | 10/2003 | Henley et al. | |
| 2003/0232084 A1* | 12/2003 | Groman et al. | 424/486 |
| 2004/0138646 A1 | 7/2004 | Walla | |
| 2005/0020487 A1 | 1/2005 | Klaus | |
| 2005/0042270 A1* | 2/2005 | Aldred | 424/449 |
| 2005/0085751 A1 | 4/2005 | Daskal et al. | |
| 2005/0131337 A1 | 6/2005 | Phipps et al. | |
| 2005/0148996 A1* | 7/2005 | Sun et al. | 604/501 |
| 2005/0165393 A1 | 7/2005 | Eppstein | |
| 2005/0209565 A1 | 9/2005 | Yuzhakov | |
| 2005/0213286 A1 | 9/2005 | Michel et al. | |
| 2005/0238704 A1 | 10/2005 | Zumbrunn et al. | |
| 2005/0273046 A1 | 12/2005 | Kwiatkowski et al. | |
| 2006/0025715 A1 | 2/2006 | Henley et al. | |
| 2006/0216339 A1 | 9/2006 | Ambron | |
| 2006/0217654 A1 | 9/2006 | Matsumura et al. | |
| 2006/0229549 A1 | 10/2006 | Hause | |
| 2006/0258973 A1 | 11/2006 | Volt | |
| 2007/0065521 A1* | 3/2007 | Venkataraman et al. | 424/646 |
| 2007/0066934 A1 | 3/2007 | Etheredge | |
| 2007/0083185 A1 | 4/2007 | Carter | |
| 2007/0083186 A1 | 4/2007 | Carter et al. | |
| 2007/0161600 A1* | 7/2007 | Helenek et al. | 514/54 |
| 2007/0224253 A1 | 9/2007 | Franklin | |
| 2007/0270732 A1 | 11/2007 | Levin et al. | |
| 2008/0027369 A1 | 1/2008 | Carter et al. | |
| 2008/0058699 A1 | 3/2008 | Hause et al. | |
| 2008/0058700 A1 | 3/2008 | Hause et al. | |
| 2008/0081051 A1 | 4/2008 | Sabin | |
| 2008/0086072 A1* | 4/2008 | Bonutti et al. | 604/21 |
| 2008/0114282 A1 | 5/2008 | Carter | |
| 2008/0154178 A1 | 6/2008 | Carter et al. | |
| 2008/0287497 A1 | 11/2008 | Anderson et al. | |
| 2009/0036821 A1 | 2/2009 | Lai | |
| 2009/0062720 A1 | 3/2009 | Anderson | |
| 2009/0124572 A1 | 5/2009 | Nelson | |
| 2009/0163597 A1 | 6/2009 | Goto | |
| 2009/0171313 A1 | 7/2009 | Yamamoto | |
| 2009/0221985 A1 | 9/2009 | Bukshpan | |
| 2009/0254018 A1 | 10/2009 | Nakayama | |
| 2009/0259176 A1 | 10/2009 | Yairi | |
| 2009/0281475 A1 | 11/2009 | Nisato | |
| 2009/0299264 A1 | 12/2009 | Matsumura et al. | |
| 2009/0299267 A1 | 12/2009 | Durand | |
| 2010/0130912 A1* | 5/2010 | Berenson | 604/21 |
| 2010/0272827 A1 | 10/2010 | Imran et al. | |
| 2010/0331759 A1 | 12/2010 | Imran | |
| 2010/0331810 A1 | 12/2010 | Imran | |
| 2010/0331811 A1 | 12/2010 | Imran | |
| 2011/0082411 A1 | 4/2011 | Imran | |

FOREIGN PATENT DOCUMENTS

| | | |
|---|---|---|
| WO | WO 2007/098058 A2 | 8/2007 |
| WO | WO 2009/158032 A1 | 12/2009 |
| WO | WO 2010/123584 A2 | 10/2010 |

OTHER PUBLICATIONS

EPO Supplementary European Search Report and European Search Opinion for application EP09770570.1 (patent EP2320885) mailed Jun. 18, 2012.
EPO Supplementary European Search Report and European Search Opinion for application EP10767443.4 (patent EP2421601) mailed Nov. 6, 2012.
PCT International Preliminary Report on Patentability for application PCT/US2010/023112 issued Aug. 11, 2011.
PCT International Preliminary Report on Patentability for application PCT/US2010/023744 issued Aug. 16, 2011.
PCT International Preliminary Report on Patentability for application PCT/US2010/040109 issued Jan. 4, 2012.
PCT International Preliminary Report on Patentability for application PCT/US2010/051541 mailed Apr. 19, 2012.
PCT International Search Report for application PCT/US2009/003837 mailed Nov. 16, 2009.
PCT International Search Report for application PCT/US2010/023112 mailed Sep. 27, 2010.
PCT International Search Report for application PCT/US2010/023744 mailed Sep. 27, 2010.
PCT International Search Report for application PCT/US2010/040109 mailed Feb. 25, 2011.
PCT International Search Report for application PCT/US2010/051541 mailed Jun. 24, 2011.
PCT Written Opinion of the International Searching Authority for applicatoin PCT/US2009/003837 mailed Nov. 16, 2009.
PCT Written Opinion of the International Searching Authority for application PCT/US2010/001227 mailed Dec. 23, 2010.
PCT Written Opinion of the International Searching Authority for application PCT/US2010/023112 mailed Sep. 27, 2010.
PCT Written Opinion of the International Searching Authority for application PCT/US2010/023774 mailed Sep. 27, 2010.

(56) References Cited

OTHER PUBLICATIONS

PCT Written Opinion of the International Searching Authority for application PCT/US2010/040109 mailed Feb. 25, 2011.
PCT Written Opinion of the International Searching Authority for application PCT/US2010/051541 mailed Jun. 24, 2011.
U.S. Appl. No. 12/459,186, Advisory Action mailed Jan. 28, 2014.
U.S. Appl. No. 12/459,186, Final Office Action mailed Sep. 18, 2013.
U.S. Appl. No. 12/459,186, Non-Final Office Action mailed Apr. 5, 2012.
U.S. Appl. No. 12/459,186, Non-Final Office Action mailed Aug. 31, 2011.
U.S. Appl. No. 12/459,862, Final Office Action mailed Jan. 29, 2013.
U.S. Appl. No. 12/459,862, Non-Final Office Action mailed Dec. 15, 2011.
U.S. Appl. No. 12/459,862, Requirement for Restriction/Election mailed Jul. 6, 2011.
U.S. Appl. No. 12/537,243, Final Office Action mailed Oct. 28, 2011.
U.S. Appl. No. 12/537,243, Non-Final Office Action mailed Apr. 8, 2011.
U.S. Appl. No. 12/537,243, Notice of Allowance mailed Jan. 19, 2012.
U.S. Appl. No. 12/658,637, Non-Final Office Action mailed Mar. 23, 2012.
U.S. Appl. No. 12/658,637, Notice of Allowance mailed Jul. 9, 2012.
U.S. Appl. No. 12/824,146, Non-Final Office Action mailed Jun. 1, 2012.
U.S. Appl. No. 12/824,147, Non-Final Office Action mailed Jun. 1, 2012.

* cited by examiner

PATCHES AND METHOD FOR THE TRANSDERMAL DELIVERY OF A THERAPEUTICALLY EFFECTIVE AMOUNT OF IRON

RELATIONSHIP TO OTHER APPLICATIONS

This application claims the benefit of priority to U.S. Provisional Application Ser. No. 61/075,720 filed Jun. 25, 2008, entitled "Patches And Methods For The Transdermal Delivery Of A Therapeutically Effective Amount Of Iron" which is fully incorporated by reference herein. This application is also related to concurrently filed U.S patent application Ser. No. 12/459,186, entitled "Patches And Methods For The Transdermal Delivery Of A Therapeutically Effective Amount Of Iron" which is fully incorporated by reference herein.

BACKGROUND

Field of the Invention

Embodiments of the invention relate to patches and methods for treating iron deficiency. More specifically, embodiments of the invention relate to patches and methods comprising the transdermal delivery of iron to an individual in need thereof.

Currently, iron is administered either parenterally or orally. Iron is administered orally via various iron preparations, including solutions, tablets or enteric coated preparations. The most common forms of oral iron preparations are ferrous sulfate and ferrous gluconate. Ferrous sulfate is less expensive and has more elemental iron in it, but is associated with more gastrointestinal side effects than ferrous gluconate. Typically, one tablet of oral iron is administered at a dose of about of about 325 mg per day, three times daily. However, one having ordinary skill in the art would recognize that a 325 mg supplement is probably made of ferrous fumarate or gluconate and actually contains only 100 mg of elemental iron per pill, the balance of the mass being the fumarate or gluconate counter iron. Moreover, only a small fraction of this dose of iron is actually absorbed.

Oral iron preparations have many disadvantages. First and foremost, they cause gastrointestinal side effects including nausea, bloating, constipation, and diarrhea. This leads to discontinuation of iron supplementation in approximately 40-66% of the patients taking such supplements. Furthermore, the absorption of iron is variable and affected by the oral ingestion of other compounds. For example, oral ingestion of food products reduces iron absorption by approximately 50%, which is problematic since many patients take iron with food in order to reduce the gastrointestinal side effects.

Secondly, many drugs are known to reduce iron absorption. For example, oral ingestion of antacids and other drugs that reduce stomach pH is known to decrease iron absorption. In turn, oral ingestion of iron also reduces the absorption of many drugs, including antibiotics.

In addition, many conditions associated with iron deficiency anemia respond poorly to oral iron supplementation, because iron cannot be properly absorbed through the cells of the gastrointestinal system. This is especially true of certain inflammatory conditions of the bowel, such as Crohn's disease. Additionally, diseases associated with functional iron deficiency, such as the anemia of renal failure are also associated with limited absorption of orally administered iron. This is also true of many other so-called "inflammatory conditions" associated with functional iron deficiency, such as those associated with rheumatoid arthritis and other autoimmune diseases as well as anemia secondary to cancer or cancer chemotherapy treatment. This is especially true in patients with these conditions, who are treated with erythropoietin, who have considerably increased demands for iron.

An alternative treatment strategy to oral iron administration is to administer iron by injection. Although iron can be injected intramuscularly, this is rarely done due to the pain associated with the injection procedure itself. Therefore, iron is typically administered intravenously when it is administered to patients via injections methods.

A variety of approaches are used to treat iron deficiency with injections of iron. In the past, only one iron preparation was available for injection, iron dextran. Although effective in correcting iron deficiency, the injection of iron dextran had several limitations. Iron dextran had to be administered over a few hours to reduce risks to patients, but despite taking this precaution, 10-15% of patients developed allergic type side effects, which occasionally resulted in the death of patients following iron dextran injection.

These side effects of iron dextran injection led to new forms of intravenous iron injection, namely using ferrous gluconate and ferrous sucrose. Equally effective, these forms of iron have become the preferred typed of iron in use today. However, most patients are treated with some type of loading regimen with several hundred milligrams of iron given over several days to weeks followed by intermittent dosing on a weekly or monthly basis of about 100 mg per injection. Methods of long-term iron administration treatment regimes via parenteral routes, such as intravenous administration, suffer from several disadvantages, most notably, localized pain at the injection site, and potentially exposing patients receiving injections to blood borne diseases.

Therefore, there is a need in the art for a more convenient and more effective form of iron supplementation for patients suffering from iron deficiency.

BRIEF SUMMARY

In various embodiments, the present invention provides for a patch for the transdermal delivery of a composition comprising a therapeutically effective amount of iron. In many embodiments, the patch is configured for transdermal iontophoretic delivery of the composition. In particular embodiments, the iron is in the form of one or more ferrous salts. One having ordinary skill in the art would recognize that the therapeutically effective amount of iron is elemental iron, which can be obtained from any of the iron-containing compounds described herein. In a related embodiment, the one or more ferrous salts are selected from the group consisting of: ferrous gluconate, ferrous chloride, ferrous sulfate, and ferrous fumarate.

Embodiments of the invention also provide for a patch for the transdermal delivery of compositions comprising a therapeutically effective amount of iron (e.g., in the form of one or more ferrous salts) and at least one agent selected from the group consisting of: a vitamin supplement, erythropoietin, and an erythropoietin stimulating agent. In a particular embodiment, the vitamin supplement is selected from the group consisting of thiamine, riboflavin, niacin, pantothenic acid, pyroxidine, biotin, folic acid, and cobalamin.

In other particular related embodiments, the invention provides for a patch for the transdermal delivery of compositions comprising a therapeutically effective amount of iron in an iron containing compound, wherein the composition further comprises a cyclodextrin.

In certain embodiments, a patch of the present invention further comprises an iron-containing composition that comprises one or more transdermal permeabilizing agents.

Thus, in various embodiments, the invention provides a patch for the transdermal delivery of a pharmaceutical composition of the present invention that comprises a therapeutically effective amount of iron from one or more iron-containing compounds, and/or one or more compounds or agents selected from the group consisting of vitamin supplements, erythropoietin stimulating agents, erythropoietin, pharmaceutically acceptable carriers, transdermal permeabilizing agents, and cyclodextrins. Further, in these and related embodiments the patch can be configured for the iontophoretic transdermal delivery of various pharamaceutical compositions and may include an electrode and a reservoir of the pharmaceutical composition.

In particular embodiments, the invention provides for a patch for the transdermal delivery of a therapeutically effective amount of iron, wherein the therapeutically effect amount of iron in the patch is in a range from about 10 mg to about 1 g of elemental iron. Further, particular embodiments provide for a patch for the iontophoretic delivery of iron in this range and other ranges described below.

In related particular embodiments, the invention provides for a patch for the transdermal delivery of a therapeutically effective amount of iron, wherein the therapeutically effect amount of iron in the patch is in the range from about 10 mg to about 300 mg of elemental iron.

In more particular embodiments, the invention provides for a patch for the transdermal delivery of a therapeutically effective amount of iron, wherein the therapeutically effect amount of iron in the patch is in the range from about 10 mg to about 100 mg of elemental iron.

In yet more particular embodiments, the invention provides for a patch for the transdermal delivery of a therapeutically effective amount of iron, wherein the therapeutically effect amount of iron in the patch is in the range from about 10 mg to about 50 mg of elemental iron.

In various embodiments, the invention also provides a method for the transdermal delivery of a composition comprising iron to an individual in need thereof. The method comprises contacting the individual with a patch comprising a composition comprising a therapeutically effective amount of iron and delivering the iron in the patch to the individual. In particular embodiments, an individual is administered iron in the form of one or more ferrous salts.

In related embodiments, an individual is administered iron in the form of one or more ferrous salts selected from the group consisting of: ferrous gluconate, ferrous chloride, ferrous sulfate, and ferrous fumarate.

The invention also provides a method for the transdermal delivery of a composition comprising iron to an individual in need thereof, The method comprises contacting an individual with a patch for the transdermal delivery of compositions comprising a therapeutically effective amount of iron (e.g., in the form of one or more ferrous salts) and at least one agent selected from the group consisting of: a vitamin supplement, erythropoietin, and an erythropoietin stimulating agent. In a particular embodiment, the vitamin supplement is selected from the group consisting of thiamine, riboflavin, niacin, pantothenic acid, pyroxidine, biotin, folic acid, and cobalamin.

In particular embodiments, the invention provides a method for the transdermal delivery of a composition comprising iron to an individual in need thereof. The method comprises contacting the individual with a patch for the transdermal delivery of compositions comprising a therapeutically effective amount of iron in an iron containing compound, wherein the composition further comprises a cyclodextrin.

In certain embodiments, methods of the invention provide for a method for the transdermal delivery of a composition comprising iron to an individual in need thereof. The method comprising contacting an individual with a patch of the present invention wherein the iron-containing composition further comprises one or more transdermal permeabilizing agents.

Thus, in various embodiments, the invention provides a method for the transdermal delivery of a composition comprising iron to an individual in need thereof. The method comprises contacting the individual with a patch comprising a pharmaceutical composition of the present invention that comprises a therapeutically effective amount of iron from one or more iron-containing compounds, and/or one or more compounds or agents selected from the group consisting of vitamin supplements, erythropoietin stimulating agents, erythropoietin, pharmaceutically acceptable carriers, transdermal permeabilizing agents, and cyclodextrins.

In particular embodiments, the invention provides a method for the transdermal delivery of a composition comprising iron to an individual in need thereof. The method comprises contacting an individual with a patch for the transdermal delivery of a therapeutically effective amount of iron, wherein the therapeutically effect amount of iron in the patch is in a range from about 10 mg to about 1 g of elemental iron.

In related particular embodiments, the present invention provides a method for the transdermal delivery of a composition comprising iron to an individual in need thereof. The method comprises contacting an individual with a patch for the transdermal delivery of a therapeutically effective amount of iron, wherein the therapeutically effect amount of iron in the patch is from about 10 mg to about 300 mg of elemental iron.

In more particular embodiments, the invention provides a method for the transdermal delivery of a composition comprising iron to an individual in need thereof. The method comprises contacting an individual with a patch for the transdermal delivery of a therapeutically effective amount of iron, wherein the therapeutically effect amount of iron in the patch is in the range from about 10 mg to about 100 mg of elemental iron.

In yet more particular embodiments, the invention provides a method for the transdermal delivery of a composition comprising iron to an individual in need thereof. The method comprises contacting an individual with a patch for the transdermal delivery of a therapeutically effective amount of iron, wherein the therapeutically effect amount of iron in the patch is in the range from about 10 mg to about 50 mg of elemental iron.

In various embodiments, the invention also provides a method for the transdermal delivery of a composition comprising iron to an individual in need thereof, comprising a step of contacting the individual with a patch comprising a composition comprising a therapeutically effective amount of iron and delivering the iron in the patch to the individual.

In related embodiments, the invention also provides a method for the transdermal delivery of a composition comprising iron to an individual in need thereof, said method comprising contacting the individual with a patch comprising a composition comprising a therapeutically effective amount of iron, delivering the composition comprising a therapeutically effective amount of iron in the patch to the individual, further comprising actively delivering the composition comprising a therapeutically effective amount of iron in the patch to the individual.

In particular embodiments, the method of actively delivering the composition comprising a therapeutically effective amount of iron in the patch can be selected from the group consisting of: thermophoresis, iontophoresis, magnetophoresis, and sonophoresis.

In particular related embodiments, the composition comprising a therapeutically effective amount of iron is delivered continuously or intermittently. In more particular related embodiments, the composition comprising a therapeutically effective amount of iron is continuously delivered for a duration of about one day to about one month. In other particular related embodiments, the composition comprising a therapeutically effective amount of iron is continuously delivered for a duration of about one day to about one week.

In yet other particular related embodiments, the composition comprising a therapeutically effective amount of iron is continuously delivered for a duration of about one day to about three days.

In yet other embodiments, the composition comprising a therapeutically effective amount of iron can continuously be delivered for a duration of about one day.

In various embodiments, the present invention also provides a method for treating and/or preventing an iron deficiency in an individual comprising contacting the individual with any one of the patches according to instant invention and delivering a therapeutically effective amount of iron to the individual, thereby preventing and/or treating an iron deficiency in an individual.

In related embodiments, a method for treating and/or preventing an iron deficiency in an individual comprises contacting the individual with any one of the patches according to the instant invention and delivering a therapeutically effective amount of iron to the individual, thereby preventing and/or treating an iron deficiency in an individual, further comprising administering a parental or oral therapeutically effective amount of iron. In particular embodiments, the administration is parenteral.

In certain particular embodiments, the parental administration can be carried out prior to contacting the individual with any one of the patches provided by embodiments of the invention. In other particular embodiments, the parental administration can be intravenous. In other related particular embodiments, the parental administration can be subcutaneous. In other particular embodiments, the administration can be oral. In certain particular embodiments, the oral administration is carried out prior to contacting the individual with any one of the patches provided by embodiments of the invention. Also, in particular embodiments the amount of delivered iron or rate of delivery of iron by any one of the patches provided by embodiments of the invention can be adjusted based on the administered parental or oral dose and vice versa.

In related embodiments, a method for treating and/or preventing an iron deficiency in an individual can also comprise administering an intravenous bolus of iron to the individual prior to the contacting the individual with any one of the patches provided by invention. The bolus can about 500 mg to 1 gram of iron.

Various embodiment of methods of the invention can be adapted for treating and/or preventing a variety of iron deficiencies. In particular embodiments, the individual has an iron deficiency without anemia. In other related embodiments, the iron deficiency is being treated in order to prevent growth retardation; cognitive disabilities, and/or mental retardation. In other certain embodiments, the iron deficiency is caused by chronic alcoholism; poor nutrition; decreased consumption of animal protein and absorbic acid; increased iron demands of pregnancy, infancy, or adolescence; malabsorption syndromes; and foods or drugs that reduce the gastrointestinal absorption of iron.

In particular embodiments, the individual has an iron deficiency anemia. In related embodiments, the iron deficiency anemia is due to blood loss caused by drugs, peptic ulcer disease, hemorrhoids, trauma, surgery, gastrointestinal bleeding, dialysis, pulmonary bleeding, uterine bleeding, menstruation, birth, urinary tract bleeding, and blood donation; primary achlorhydia, secondary achlorhydia secondary to use of compounds that reduce stomach acid pH; gastrointestinal disease; Crohn's disease; ulcerative colitis; sprue; gastric bypass surgery; pernicious anemia; intestinal parasites; hookworm infection; trichuriasis; functional iron deficiency resulting from the use of erythropoietic stimulating agents; inflammatory diseases autoimmune diseases; renal failure; cancer; and beta thalassemia.

In certain related embodiments, the individual has an iron deficiency characterized by microcytosis of red blood cells, a hemoglobin iron binding capacity of less than 20%, ferritin levels less than 10 µg/L, or transferrin iron saturation levels less than 20%. In other related embodiments, the individual has a functional iron deficiency with ferritin levels less than 100 µg/L.

In related embodiments, a method for treating and/or preventing an iron deficiency in an individual includes actively delivering the composition comprising a therapeutically effective amount of iron in the patch to the individual. In particular embodiments, the method of active delivery is selected from the group consisting of: thermophoresis, iontophoresis, magnetophoresis, and sonophoresis. In each case, the patch can be adapted for the particular mode of delivery. For example, the patch can be adapted for transdermal iontophoretic delivery by including in the patch an electrode and reservoir of iron containing compound.

In various embodiments, the methods of the inventions can be adapted for treatment/prevention of iron deficiency of an individual who is a child, infant, or neonate. In these and related embodiments, the child, infant or neonate can be administered a therapeutically effective amount of iron from about 1 mg to 100 mg. In related embodiments, the child, infant, or neonate can be delivered a therapeutically effective amount of iron continuously for a duration of about one day to about seven days. In certain embodiments, the therapeutically effective amount of iron can actively be delivered to these individuals using one or more embodiments of the patches described herein. In these and related embodiments, the method of active delivery can include thermophoresis, iontophoresis, magnetophoresis, sonophoresis and combinations thereof. The patch can be adapted for each method or combination of methods. Embodiments of the patch for iontophoretic delivery can include one or more of an active electrode assembly or a return electrode assembly.

Further details of these and other embodiments and aspects of the invention are described more fully below with reference to the attached figures.

BRIEF DESCRIPTION OF THE DRAWINGS

FIGS. 10a-10d show use of the micro-needle array patch to create micro-channels in the skin; FIG. 10e shows application of the transdermal patch. FIG. 10f shows application of a transdermal iontophoretic patch.

DETAILED DESCRIPTION OF THE INVENTION

Figure 1:
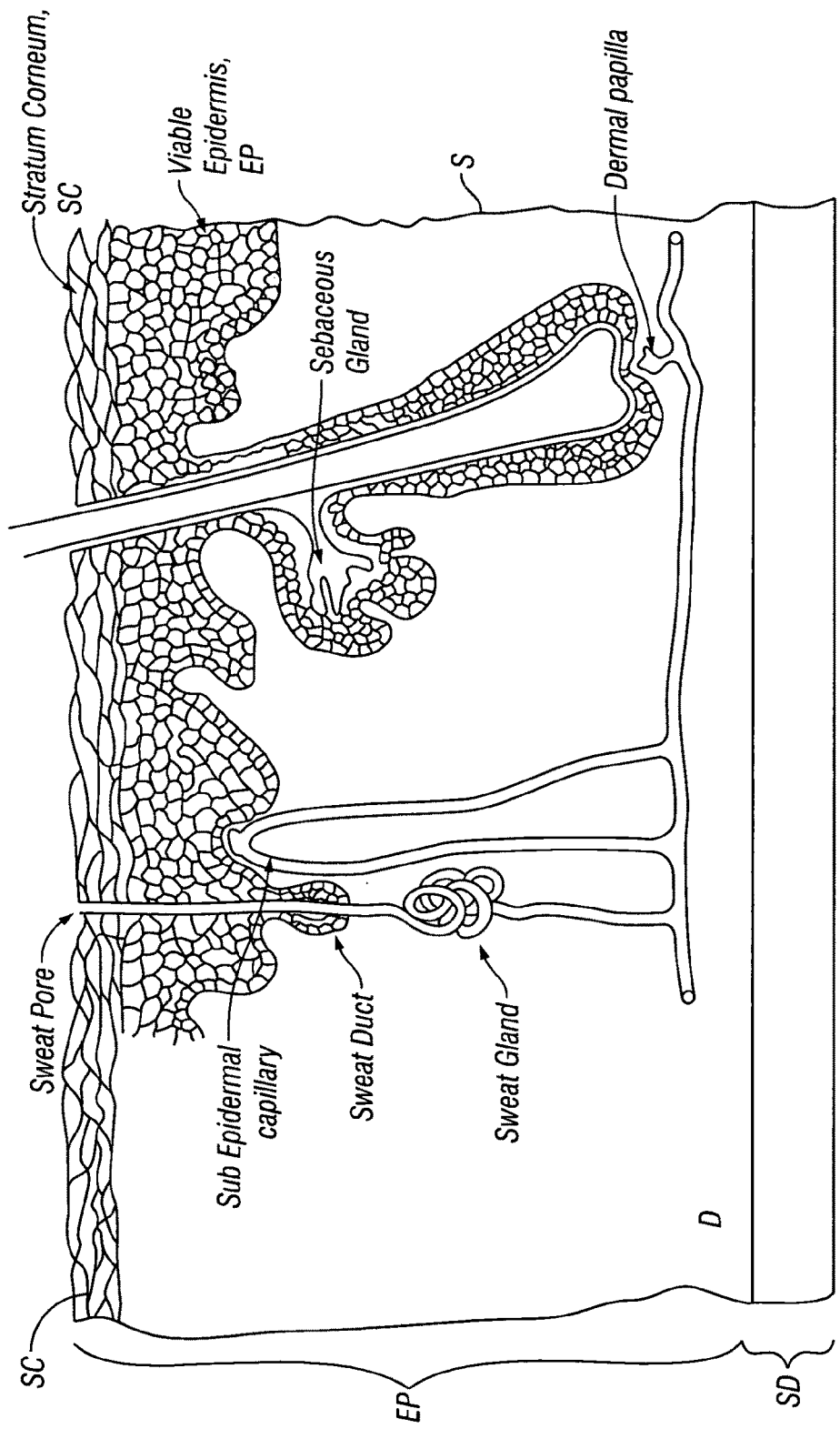
FIG. 1 is a cross sectional view showing the three main layers of the skin, the epidermis, the dermis and subcutaneous tissue as well as the passageways into the skin.

Embodiments of the invention provide devices and methods for the transdermal delivery of a composition comprising a therapeutically effective amount of iron. Embodiments of the invention are particularly useful for the treatment of iron deficiency including iron deficiency anemia. Accordingly, in various embodiments, the invention provides for the delivery of a composition comprising a therapeutically effective amount of iron to an individual in need thereof. As used herein, the term "therapeutically effect amount" means the amount of iron in the form of an iron-containing compound, such as for example, a ferrous salt, that when administered to an individual for treating a state, disease, disorder or condition associated with or caused by an iron deficiency is sufficient to effect such treatment. The "therapeutically effective amount" will vary depending on the particular state, disease, disorder or condition being treated and its severity and the age, weight, physical condition and responsiveness of the individual to be treated. Thus one or more of these parameters can be used to select and adjust the therapeutically effective amount of iron. Also, the amount can be determined using pharmacologic methods known in the art such as dose response curves.

The term "treating" or "treatment" of a state, disorder or condition as used herein means: (1) preventing or delaying the appearance or development of the clinical symptoms of the state, disease, disorder or condition associated with or caused by an iron deficiency in an individual that may be afflicted with or predisposed to the state, disease, disorder or condition but does not yet experience or display clinical or subclinical symptoms of the state, disease, disorder or condition, (2) inhibiting the state, disease, disorder or condition associated with or caused by an iron deficiency, e.g., arresting or reducing the development of the state, disease, disorder or condition associated with or caused by an iron deficiency or at least one clinical or subclinical symptom thereof, or (3) relieving or ameliorating the state, disease, disorder or condition associated with or caused by an iron deficiency, e.g., causing regression or amelioration of the state, the state, disease, disorder or condition associated with or caused by an iron deficiency or at least one of its clinical or subclinical symptoms. The benefit to a subject to be treated is either statistically significant or at least perceptible to the patient or to the physician (e.g., an increased hematocrit as measured using clinical analytical methods known in the art). Thus, the methods and transdermal delivery devices contemplated herein are suitable to treat any form of iron deficiency.

Transdermal Delivery

Embodiments of the invention contemplate, in part, a transdermal device to deliver a composition comprising a therapeutically effective amount of iron (e.g., in the form of ferrous salts) to an individual in need thereof. In particular embodiments, the individual is a mammal, and in related embodiments, the mammal is a human. In particular embodiments, the human is an athlete, pregnant female, pre-menopausal female, post-menopausal female, adolescent, child, infant, or neonate. In certain embodiments, the individual can be selected from the group consisting of an adolescent, child, infant, and neonate.

Referring now to FIG. 1, human skin S comprises the dermis D, sub dermis SD and the epidermis E. The epidermis has several layers of tissue, namely, stratum corneum SC, stratum lucidum, stratum granulosum, stratum spinosum, and stratum basale (identified in order from the outer surface of the skin inward). The stratum corneum presents the most significant hurdle in transdermal delivery of medications. The stratum corneum is typically about 10-15 µm thick, and it consists of flattened, keratised cells (corneocytes) arranged in several layers. The intercellular space between the corneocytes is filled with lipidic structures, and may play an important role in the permeation of substances through skin (Bauerova et al., Chemical enhancers for transdermal drug transport, European Journal of Drug Metabolism and Pharmacokinetics, 2001, 26(1/2): 85-94). The rest of the epidermis below the stratum corneum is approximately 150 µm thick. The dermis D is about 1-2 mm thick and is located below the epidermis. The dermis D is innervated by various capillaries as well as neuronal processes.

One having ordinary skill in the art would understand that transdermal administration of pharmaceuticals has been the subject of intense research efforts to provide an effective adjunctive route of administration to parenteral and oral delivery of particular pharmaceutical compositions or compounds. For example, embodiments of the invention provide methods wherein an individual suffering from an iron deficiency can be administered a therapeutically effective amount of iron in a composition, e.g., in the form of a pharmaceutical composition comprising one or more ferrous salts, via oral or parenteral routes in order to establish normal ranges of iron levels rapidly, and then that individual can further be administered a therapeutically effective amount of iron obtained from one or more iron-containing compounds in a composition (e.g., ferrous salts) through a transdermal delivery device in order to maintain normal and/or healthy iron levels over a sustained period of time, e.g., days, weeks or months.

One having ordinary skill in the art would understand that transdermal delivery is often the preferred mode of long-term administration for compositions comprising iron, because repeated or long-term use of parenteral routes of iron administration often cause localized pain, and potentially expose patients receiving injections to blood borne diseases. In addition, treating an individual suffering from an iron deficiency strictly by oral administration of iron-containing compositions comprising ferrous salts on a long-term basis is often undesirable due to the gastrointestinal side effects associated with the oral administration of iron, including nausea, bloating, constipation, and diarrhea. The bioavailability of orally administered iron-containing compositions is also an issue due to the co-consumption of food with said compositions, drugs that reduce stomach pH, or poor intestinal absorption of iron associated with particular diseases, disorders, or conditions that affect iron absorption, e.g., Crohn's disease.

In particular embodiments, the transdermal delivery of a composition comprising a therapeutic amount of iron as described herein throughout attempts to increase the therapeutic efficacy of said compositions by improving the permeability of the stratum corneum to embodiments of the composition. In related embodiments, the present invention provides methods of transdermal delivery that are directed at administering pharmaceutical compositions that are incorporated into a patient's circulatory system, and thus, allow systemic administration of the composition through the skin.

In some embodiments, the methods and/or transdermal delivery devices of the present invention comprise chemical enhancing agents that increase the permeability of molecules through the skin.

In other embodiments, the administration of a therapeutically effective amount of iron in the form of one or more ferrous salts involves using embodiments of a mechanical apparatus in order to bypass or ablate portions of the stratum corneum. In related embodiments, the methods of the invention provide for the use of ultrasound or iontophoresis to facilitate the permeation of compositions comprising iron (e.g., ferrous salts) through the skin.

Various embodiments of the invention provide transdermal delivery devices that are configured to deliver a pharmaceutical composition comprising at least one iron-containing compound, typically in the form of one or more ferrous salts, through the skin so that an iron-containing compound may pass to the capillary bed in the dermis where the iron may be systemically incorporated into the individual being treated in order to achieve a therapeutic effect.

Figure 2:
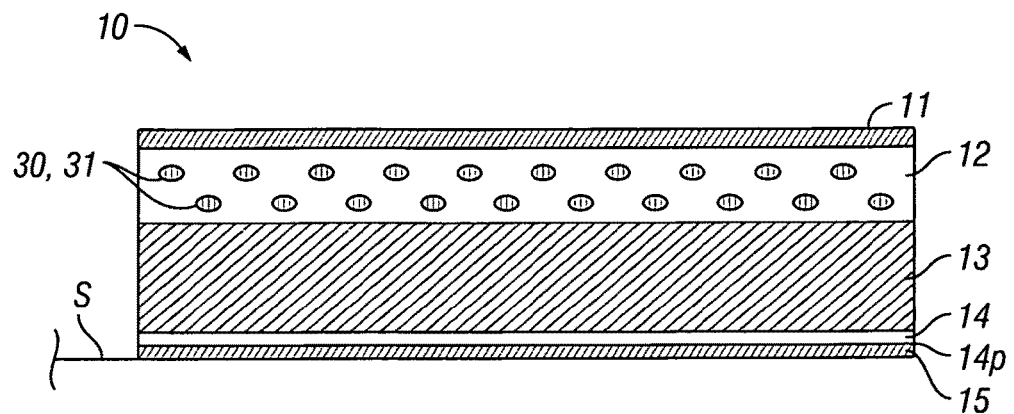
FIG. 2 is a lateral view of an embodiment of a system including a patch for the transdermal iontophoretic delivery of various therapeutic agents.

Referring now to FIG. 2, various embodiments of the invention provide transdermal delivery devices in the form of a transdermal patch 10 or related device, which is configured to deliver a composition 30 comprising a therapeutically effective amount of iron either in a manner which: (1) controls the rate of drug delivery to the skin S or (2) allows the skin S to control the rate of drug absorption. In many embodiments, patch 10 is configured for transdermal iontophoretic delivery and can include an active electrode assembly and a counter electrode assembly as is described below.

Embodiments of transdermal patch 10 are desirably configured for the transdermal delivery of a composition 30 comprising a therapeutically effective amount of iron from one or more iron-containing compounds (e.g., ferrous salts) to provide prevention, amelioration, and/or treatment to an individual in need thereof. Embodiments of transdermal patch 10 can include (i) a backing layer 11; (ii) a reservoir layer or compartment 12; (iii) a controlling membrane or non controlling micro-porous membrane 13; (iv) an adhesive film 14; and (v) a release liner 15. Reservoir layer or compartment 12 contains or can be loaded with a pharmaceutical composition 30 comprising a therapeutically effective amount of iron from at least one iron-containing compound 31. In a particular embodiment, the at least one iron-containing compound 31 is in the form of a ferrous salt as described elsewhere herein. The pharmaceutical composition may further comprise as described herein: a pharmaceutically effective carrier, vitamin supplement, erythropoietin, an erythropoietin stimulating agent, and/or a transdermal permeabilizing agent.

One having ordinary skill in the art is familiar with the methods used to manufacture and use the transdermal delivery devices of the present invention. For example, the backing layer 11, reservoir layer 12, controlling membrane 13, adhesive 14 and release liner 15 can be formed using conventional teachings in the art such as those referred to in U.S. Pat. No. 6,818,226 (Dermal penetration enhancers and drug delivery systems involving same); U.S. Pat. No. 6,791,003 (Dual adhesive transdermal drug delivery system); U.S. Pat. No. 6,787,149 (Topical application of opioid analgesic drugs such as morphine); U.S. Pat. No. 6,716,449 (Controlled release compositions containing opioid agonist and antagonist); U.S. Pat. No. 5,858,393 (Transdermal formulation); U.S. Pat. No. 5,612,382 (Composition for percutaneous absorption of pharmaceutically active ingredients); U.S. Pat. No. 5,464,387 (Transdermal delivery device); U.S. Pat. No. 5,023,085 (Transdermal flux enhancers in combination with iontophoresis in topical administration of pharmaceuticals; U.S. Pat. No. 4,891,377 (Transdermal delivery of the narcotic analgesics etorphine and analogs); U.S. Pat. No. 4,654,209 (Preparation of percutaneous administration), each of which is incorporated by reference herein in its entirety.

Figure 3:
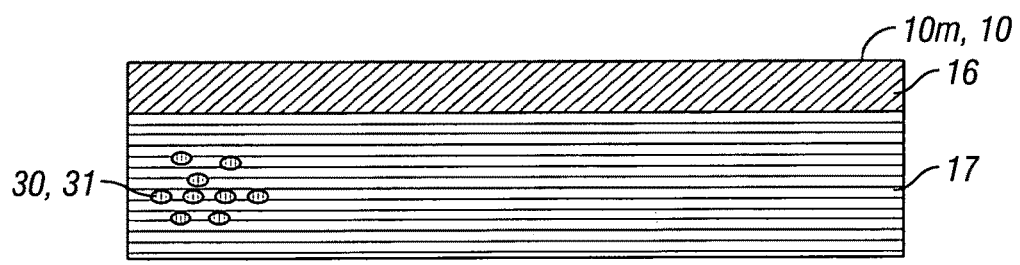
FIG. 3 is a lateral view showing an embodiment of a transdermal patch.

Referring now to FIG. 3, embodiments of transdermal patch 10 may include various structural components known in the art. For example, in the case of an adhesive matrix patch 10m (also described herein as matrix patch 10m), a distal backing 16 is often laminated to a matrix polymer layer 17. Such a distal backing 16 defines the side of the matrix patch 10m that faces the environment, i.e., distal to the skin or mucosa. The backing layer functions to protect the matrix polymer layer and iron-containing composition and to provide an impenetrable layer that prevents loss of iron composition to the environment. Thus, the material chosen for the backing is desirably compatible with the polymer layer, iron-containing compounds, and other components such as a transdermal permeabilizing agent, and is desirably minimally permeable to any components of the matrix patch. In one aspect, the backing may be opaque to protect components of the matrix patch from degradation from exposure to ultraviolet light. In another aspect, the backing may be transparent in order to minimize the visibility of the patch when applied. Also, the backing is desirably capable of binding to and supporting the polymer layer, and also desirably pliable enough to accommodate the movements of a person using the matrix patch.

Suitable materials for the backing include, without limitation: metal foils, metalized polyfoils, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. Additionally, the backing may include various foams, such as closed cell foams. Examples may include, without limitation, polyolefin foams, polyvinyl chloride foams, polyurethane foams, polyethylene foams, etc. In one aspect of the invention, the backing layer may have a thickness of about 0.0005 to 0.1 inch.

In various embodiments, transdermal patch 10 or other related transdermal delivery device can include a pharmaceutically acceptable carrier intended to contain one or more iron-containing compounds and any other components included in the formulation of a composition according to the present invention. A number of pharmaceutically acceptable carriers are known to those of ordinary skill in the art and may be used in connection with the present invention.

Embodiments of patch 10 may also include a release liner 15 may that is removably coupled (e.g., by pealing) to the proximal side 14p (the side to adhered to the skin) of an adhesive layer 14. Such a liner 15 provides many of the same functions as the backing layer 11, prior to adhesion of the patch 10 to the skin. In use, the release liner 15 is peeled from the adhesive layer 14 just prior to application and then discarded. The release liner 14 can be made of the same materials as the backing layer, or other suitable films coated with an appropriate release agent known in the art.

Figure 4:
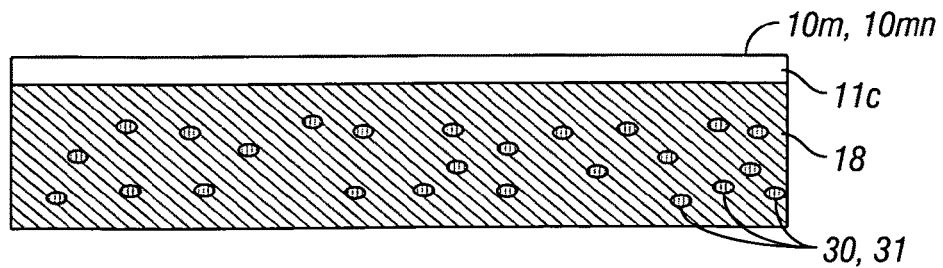
FIG. 4 is a lateral view showing an embodiment of a transdermal patch having a monolithic construction.
Figure 5:
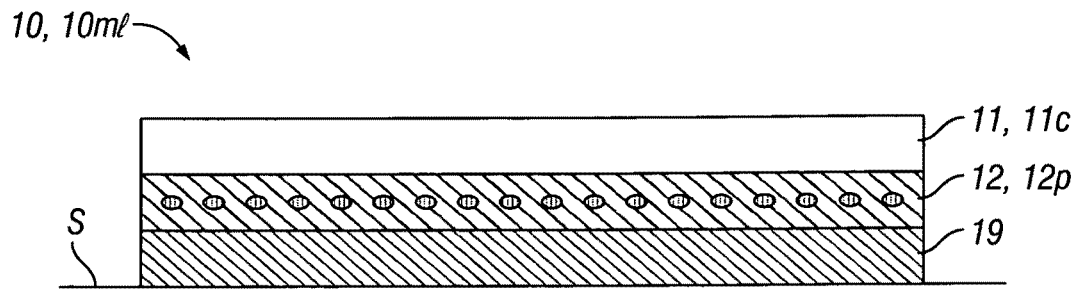
FIG. 5 is a lateral view showing an embodiment of a multilayer transdermal patch including a rate controlling member.
Figure 6:
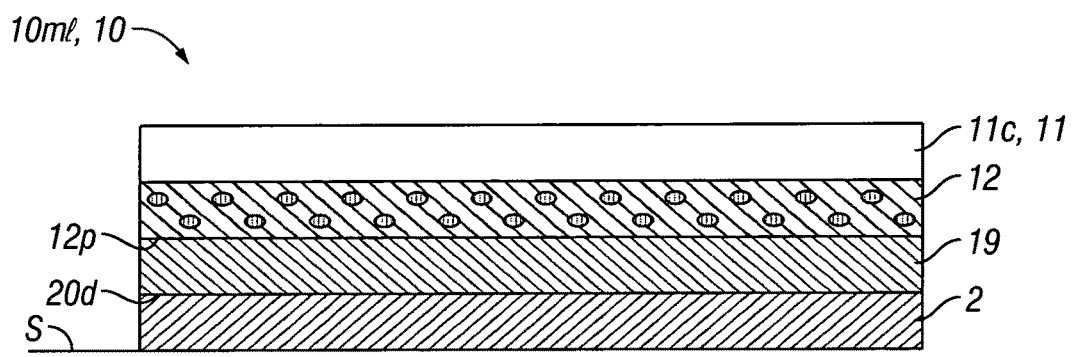
FIG. 6 is a lateral view showing an embodiment of a multilayer transdermal patch including a rate controlling member positioned between the reservoir and a delivery layer.

Referring now to FIGS. 4-6, embodiments of the invention contemplate various structural arrangements for transdermal matrix patches 10m including patches configured for iontophoretic delivery. For example, in an embodiment shown in FIG. 4, matrix patch 10m can have monolithic arrangement 10ma where the composition 30 comprising an iron-containing compound 31 is contained directly in a single pressure sensitive adhesive layer 18. Layer 18 is integral or coated onto a carrier layer 11c, analogous to backing layer 11. In related embodiments, patch 10m can also include one or more polymeric reservoirs (not shown) in addition to a pressure sensitive adhesive layer 18. Other embodiments of patch 10m can comprise a multilayer/laminate patch 10ml as shown in the embodiment of FIG. 5. Embodiments of multilayer patch 10ml can include a rate controlling member 19 and/or a delivery layer 20. Member 19 and/or layer 20 can be integral or attached to carrier layer 11c. Typically, a rate controlling member 19 is located between a reservoir layer 12 and the skin S. In those embodiments also including a delivery layer 20 and a reservoir layer 12, the rate controlling member 19 may be adhered between a proximal side 12p (the side closer to the skin) of the reservoir layer 12, and a distal side 20s (the side farther from the skin) of the delivery layer 20 as is shown in the embodiment of FIG. 6. The rate controlling member 19 is configured to meter or control, the rate at which the iron containing composition or other drug and/or penetration enhancer migrates from the reservoir layer into the delivery layer 20. As noted herein, in one aspect of the present invention, one or more transdermal permeabilization agents may be used to increase the delivery rate of the drug, and thus be used to vary other parameters, such as patch size, etc.

In one aspect, the carrier layer 11c used in a matrix patch 10m can be a biocompatible polymer. Various general categories of biocompatible polymers are known, including, without limitation, rubbers; silicone polymers and copolymers; acrylic polymers and copolymers; and mixtures thereof. In one aspect, the biocompatible polymer can be a rubber, including natural and synthetic rubbers. One specific example of a useful rubber is a plasticized styrene-rubber block copolymer. In another aspect, the biocompatible polymer can include silicone polymers, polysiloxanes, and mixtures thereof. In yet another aspect, the biocompatible polymer can include acrylic polymers, polyacrylates, and mixtures thereof. In a further aspect, the biocompatible polymer can include vinyl acetates, ethylene-vinyl acetate copolymers, polyurethanes, plasticized polyether block amide copolymers, and mixtures thereof. In one specific aspect, the biocompatible polymer can include an acrylic copolymer adhesive such as copolymers of 2-ethylhexyacrylate and n-vinyl pyrrolidone adhesives.

In one aspect, the biocompatible polymer can be suitable for long-term (e.g., greater than 1 day, maybe about 3-4 days, or longer such as 7 days, or even 1-4 weeks) contact with the skin. In another aspect, the biocompatible polymer of the carrier is suitable for a short-term administration (e.g., for a few minutes to a few hours, less than or equal to 1 day). Such biocompatible polymers must be physically and chemically compatible with the iron-containing compounds of the present invention, and with any carriers and/or vehicles or other additives incorporated into the formulation. In one aspect, the biocompatible polymers of the carrier can include polymeric adhesives. Example of such adhesives can include without limitation, acrylic adhesives including cross-linked and uncross-linked acrylic copolymers; vinyl acetate adhesives; natural and synthetic rubbers including polyisobutylenes, neoprenes, polybutadienes, and polyisoprenes; ethylenevinylacetate copolymers; polysiloxanes; polyacrylates; polyurethanes; plasticized weight polyether block amide copolymers, and plasticized styrene-rubber block copolymers or mixtures thereof. In a further aspect of the invention, contact adhesives for use in the carrier layer 11c can be acrylic adhesives, such as DuroTak.™. 87-2888 adhesive (National Starch & Chemical Co., Bridgewater, N.J.); and polyisobutylene adhesives such as ARcare.™. MA-24 (Adhesives Research, Glen Rock, Pa.) and ethylene vinyl acetate copolymer adhesives. In yet another aspect, gel-type or "hydrogel" adhesives are contemplated for use. See for example, U.S. Pat. No. 5,827,529 which is incorporated herein by reference. Those of ordinary skill in the art will appreciate that the specific type and amount of adhesive polymer used may be selected depending upon the desired specific characteristics of the final product (e.g., size and intended wear time of the patch as well as the intended location, e.g., arm vs. leg).

Various embodiments of transdermal matrix patches 10m, including those configured for transdermal iontophoretic delivery, can have a range of sizes with the size based on the desired dosage of elemental iron in the patch and the desired rate of delivery as well as other factors (e.g., delivery site, skin type, use of permeabilizing agent, etc). In one aspect, transdermal patches 10, including patches configured for iontophoretic delivery, may have a size ranging from about 0.5 cm$^2$ to about 200 cm$^2$ in surface area. In another aspect, transdermal patches 10 may have a size from about 5 cm$^2$ to about 75 cm$^2$ in surface area. In yet another aspect, transdermal patches 10 may have a size ranging from about 10 cm$^2$ to about 100 cm$^2$ in surface area. In a further aspect, transdermal patches may have a size ranging from about 50 cm$^2$ to about 100 cm$^2$ in surface area. In yet a further aspect, transdermal patches may have a size ranging from about 0.5 cm$^2$ to about 100 cm$^2$ in size. In an additional aspect, transdermal patches may have a size ranging from about 100 cm$^2$ to about 200 cm$^2$ in surface area. In yet an additional aspect, transdermal patches 10 may have a size ranging from about 10 cm$^2$ to about 50 cm$^2$ in surface area.

Various embodiments of transdermal patches 10 including those configured for transdermal iontophoretic delivery described herein can be configured to provide short, intermediate, and long durations of administration of a pharmaceutical composition comprising at least one iron-containing compound. One having ordinary skill in the art would recognize that the duration of administration can be selected through the selection of a number of variables, including, but not limited to the choice of transdermal permeabilizing agent, type of controlling or non-controlling micro-porous membrane in the patch, and the mode in which the composition is delivered (i.e., actively or passively).

In one embodiment, a transdermal patch delivers a pharmaceutical composition of the present invention passively through the pressure of the applied patch. In another embodiment of passive delivery, the transdermal patch may constitute a so-called "drug in adhesive" or matrix patch 10m in which there is no reservoir layer but instead an iron-containing composition is intimately distributed in an appropriate pressure sensitive adhesive such as but not limited to the DURO-TAK polyacrylates.

Another embodiment of a passive delivery approach for a pharmaceutical composition including an iron-containing compound exploits a natural transport mechanism in the skin to carry drugs across without disrupting the skin surface. This approach is based on the observation that phosphorylated vitamin E penetrates skin almost ten times faster than vitamin E itself. Thus in an embodiment the iron-containing composition can be encapsulated within a shell of phosphorylated vitamin E, so as to create phosphorylated vitamin E nanospheres. These vitamin E nanospheres then enable the iron-containing composition to be efficiently carried across the skin. Continuous delivery over an extended period is then achievable.

Various embodiments of the invention also contemplate the creation of micro-channels in the stratum corneum and/or other layers of skin (e.g., the epidermis) for enhancing the transdermal delivery of an iron containing compound or other pharmaceutical composition. The micro-channels can be created using several different approaches including by mechanical means, (e.g., through the use of micro-needles or other tissue penetrating element), electrical means (e.g., by an electrostatic discharge to the skin); acoustical means (e.g., the use of high frequency ultrasound delivered to the skin); and chemical means (e.g., the use of permeabilizing agents). Various embodiments of the invention also contemplate that such methods for the creation of micro-channels can be used with a number of embodiments of transdermal patches 10, including embodiments configured for transdermal iontophoretic delivery. The particular means for creation of the micro-channels can be selected and adjusted as needed based on several factors including the desired amount and rate of iron delivery or other pharmaceutical as well as various patient characteristics and the type and degree of iron deficiency.

Figure 7:
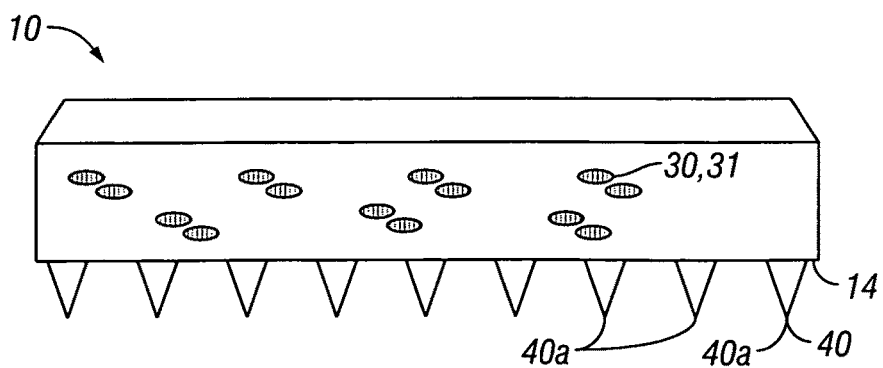
FIG. 7 is a lateral view showing an embodiment of a transdermal patch including an array of micro-needles.
Figure 8:
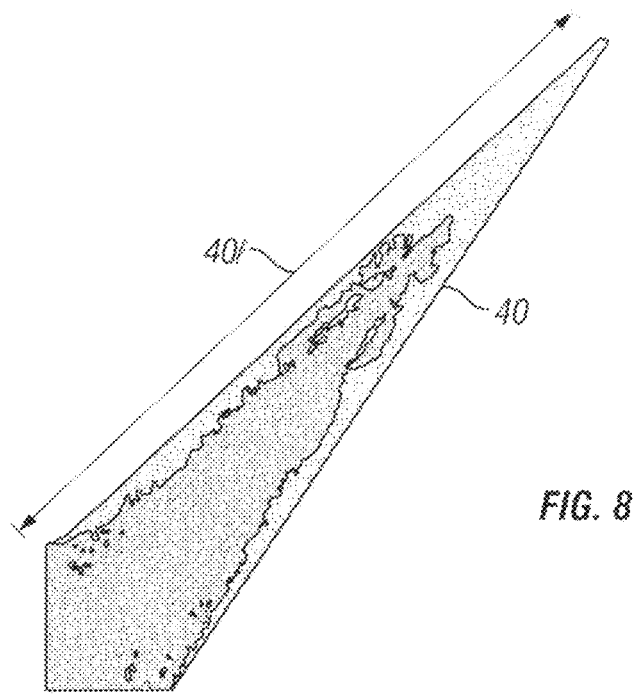
FIG. 8 is a perspective view of an embodiment of a microneedle.
Figure 9:
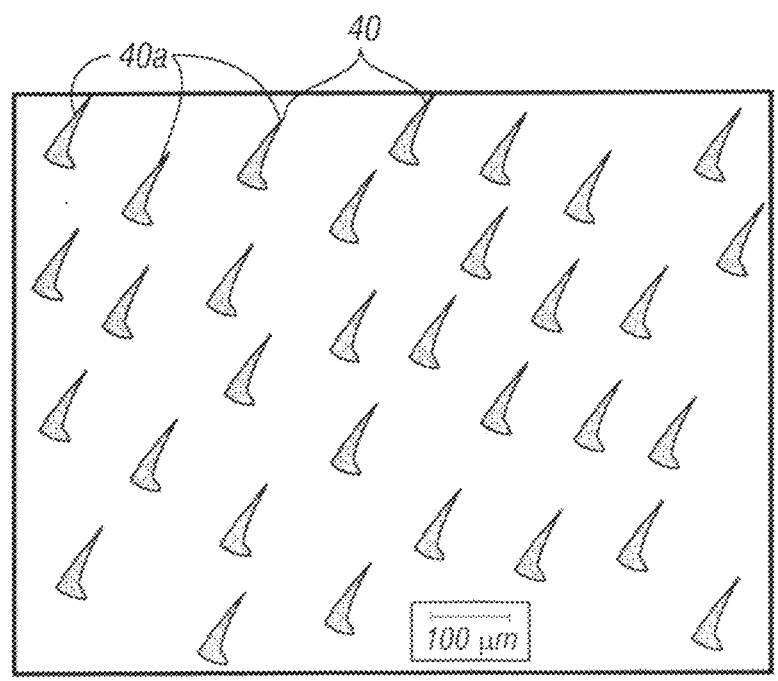
FIG. 9 is a perspective view of an embodiment of an array of micro needles.

Referring now to FIGS. 7-9, in particular embodiments of the invention, the transdermal patch 10 other transdermal device 10 can comprise an array 40a of micro-needles 40 positioned on the skin contacting side 10p of a transdermal patch 10 as is shown in the embodiment of FIG. 7. The length 40l of the micro-needle(s) is desirably configured to be long enough to penetrate the stratum corneum (e.g., the outer 10-15 µm of the skin) and yet short enough so as not to stimulate the nerves deeper in the skin, e.g., such as those found deeper in the epidermis and dermis. Suitable lengths 40l for the micro-needles can be in the range from 10 to 150 µm, 10 to 15, 25-50, 75-100 and in a preferred embodiment 100-150 µm, the latter range being preferred in that it provides additional length to account for the uneven surface topology of the skin including wrinkles, hairs etc. Needle array 40a can be fabricated using various micro-fabrication techniques known in the art including a combination of photolithography and etching techniques known in the art such as reactive ion etching. Examples of a micro-needle 40 and micro-needle array 40a are shown in the embodiment of FIGS. 8 and 9. The array can be can be attached to patch 10 using various adhesive or other joining methods known in the art or can be fabricated directly onto the patch 10. Also needle array 40a can be configured such that it can be pressed a desired depth into the skin with a force of no more than about 10 Newtons. Further description of micro-needles and micro-needle fabrication techniques can be found in a paper by Henry et al., "Microfabricated Microneedles: A Novel Approach to Transdermal Drug Delivery", J. Pharm. Sci., vol. 87: 922-925 (1998), which is incorporated by reference herein in its entirety.

Embodiments of the invention contemplate several approaches for using micro-needles as a means to deliver or enhance transdermal delivery of iron containing and other pharmaceutical compositions. The array of micro-needles creates a plurality of micro-channels in the skin, through which the iron containing or other composition can permeate. In one embodiment, the iron-containing composition can be stored in a lumen or hollowed out section of the micro-needles.

Figure 10A:
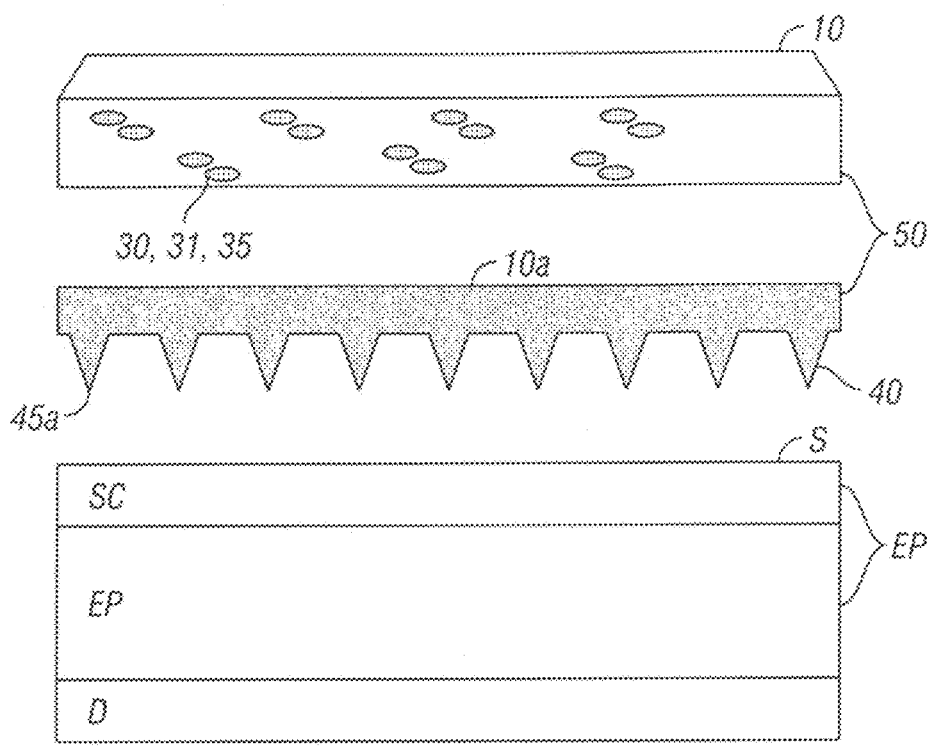
FIGS. 10a-10f are lateral views of an embodiment of a system for transdermal delivery of iron or other therapeutic agent comprising a transdermal delivery patch and a micro-needle array patch or other related device.
Figure 10B:
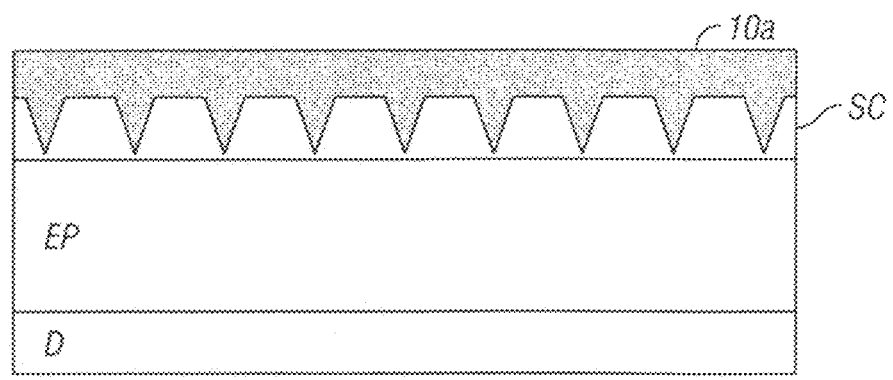
Figure 10C:
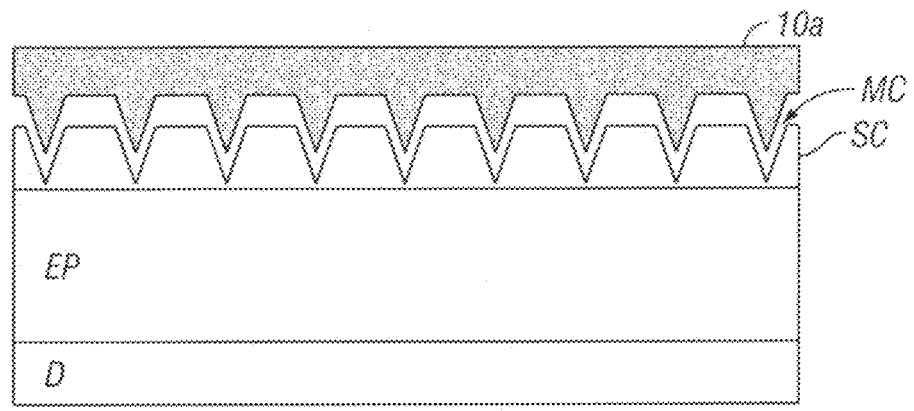
Figure 10D:
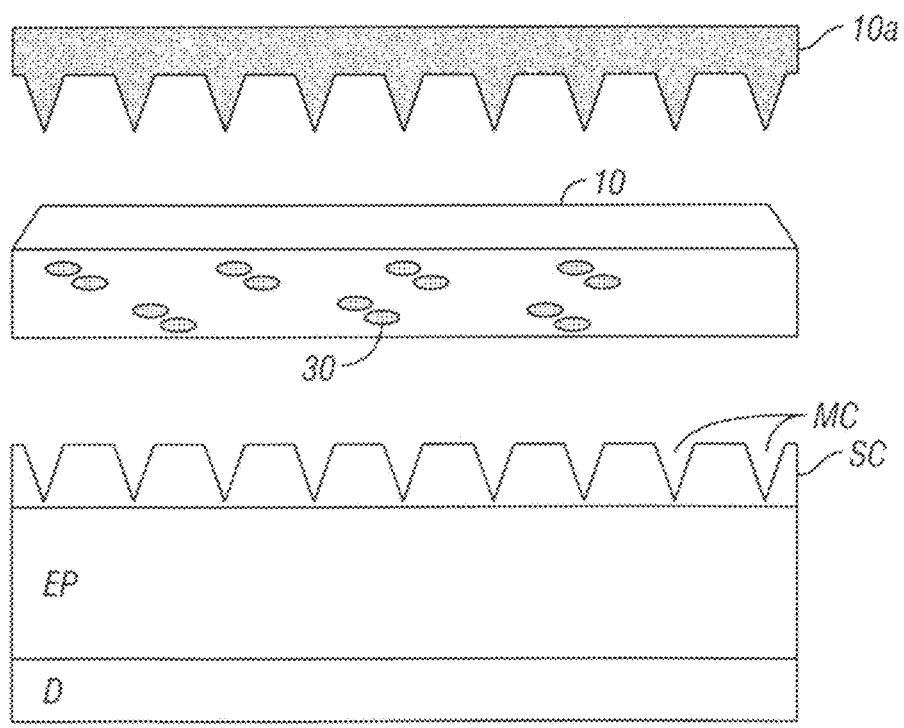
Figure 10E:
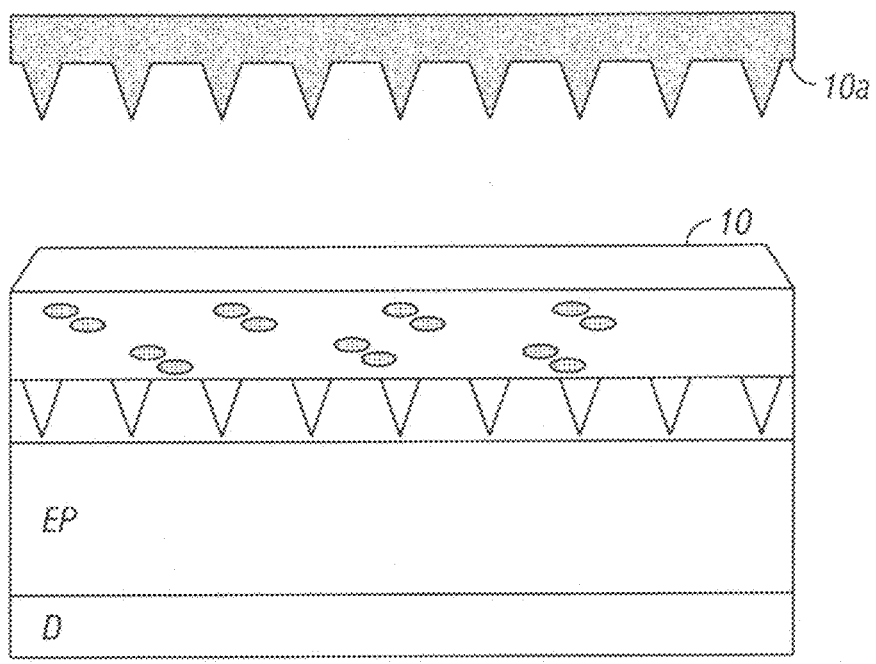
Figure 10F:
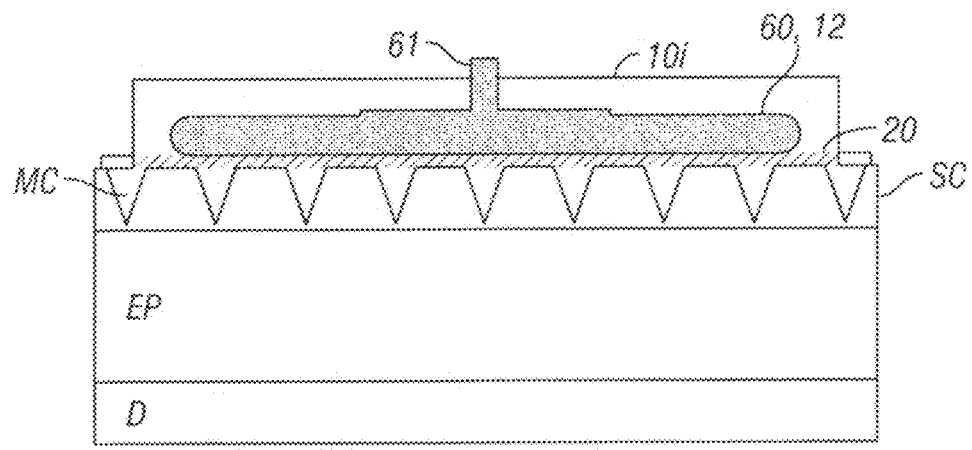

In other embodiments, after the micro-channels are created the array of micro needles can be removed from the skin and a separate transdermal patch can be applied. Accordingly, referring now to FIGS. 10a-10f, embodiments of the invention contemplate a system 50 for creating micro-channels MC and then transdermally delivering an iron compound 31 or therapeutic agent through the micro-channels. The system 50 comprises one more embodiments of a transdermal delivery patch 10 and a patch 10a having an array 40a of micro-needles 40 having a selectable length to only penetrate the stratum corneum SC. In use, patch 10a is applied to the skin and left on for a brief period of time (e.g., seconds to minutes) so as to create micro-channels MC. After patch 10a is removed, a delivery patch 10 is applied to skin and iron or other compound 31 is delivered into the skin through micro-channels MC which provide for enhanced transdermal delivery of the compound. In many embodiments, transdermal patch 10 can be a transdermal iontophoretic delivery patch 10i with iontophoretic transport occurring through micro-channels MC as is shown in the embodiment of FIG. 10f. In these and related embodiments, transport of compound 31 through micro-channels MC (which have a greatly reduced resistance to transport/diffusion of the compound compared to an intact stratum corneum) serves to greatly enhance the rate and amount of compound 31 delivered into the skin because of the reduced diffusional resistance.

In still other embodiments for the creation of micro-channels, patch 10 can include an array of metallic filaments and a separate battery-operated electrical activator. A momentary pulse of current applied to the filaments through the activator creates numerous micro-channels through the stratum corneum allowing the drug to subsequently permeate in a continuous manner.

Figure 11:
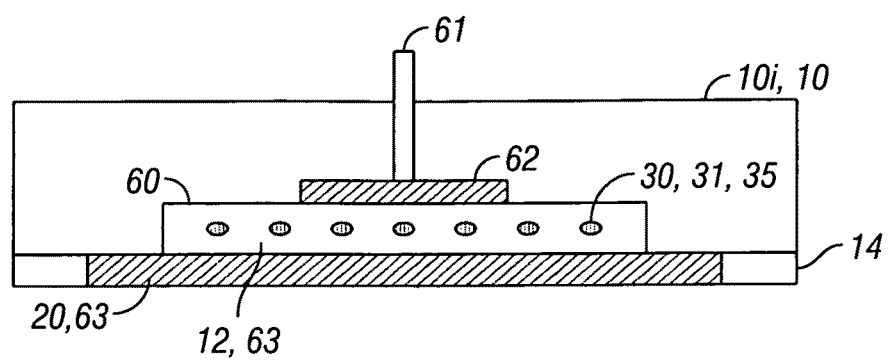
FIG. 11 is a lateral view of an embodiment of a transdermal iontophoretic patch.
Figure 12:
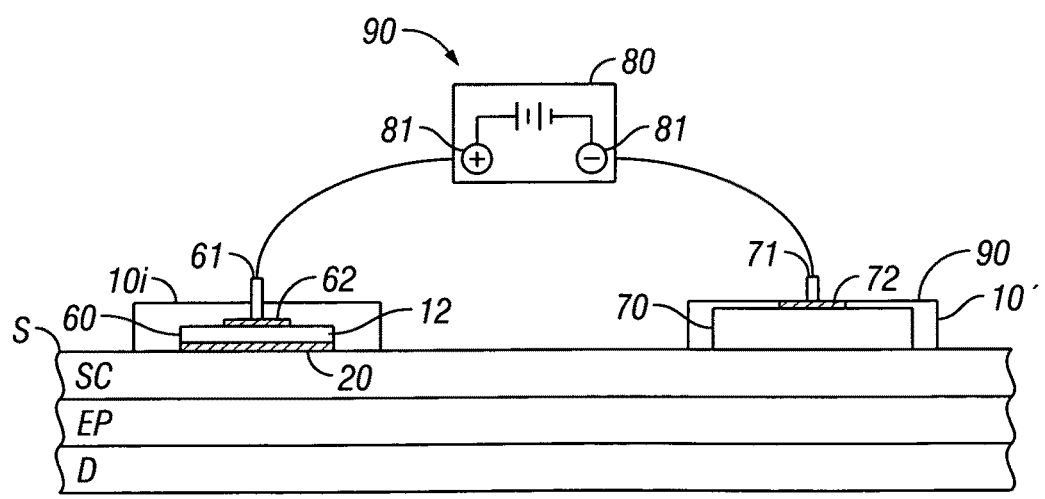
FIG. 12 is a lateral view of an embodiment of a transdermal iontophoretic delivery system.

In many embodiments, transdermal patch 10 can be configured to use iontophoresis in order to drive the iron-containing compound 31 through the skin of the individual being treated. Referring now to FIGS. 11 and 12, such embodiments of a transdermal iontophoretic patch 10i include an active electrode assembly 60 as well as other components of patch 10 described herein, e.g. an adhesive layer 14, etc. Active electrode assembly 60 can include an electrical connector 61, an electrode element 62 (also described as electrode 62) and one or more of a reservoir 12 or delivery layer 20. Connector 61 is electrically coupled to electrode 62 and configured to be coupled to an electrical power source 80. Electrode 62 comprises a metal or other conductive material, and is directly or operatively electrically coupled to one or more of reservoir 12 or delivery layer 20. One or both of reservoir 12 and delivery layer 20 can comprise an iontophoretic chamber 63 which contains iron-containing compound 31 or other active agent 35. Transdermal iontophoretic patch 10i can use an electromotive force and/or current to transfer an active agent 35 to the skin or other biological interface (e.g., a mucus membrane) and the like, by using a small electrical charge applied to an iontophoretic chamber containing a similarly charged active agent and/or its vehicle. The active agent 35 can include a charged substance, an ionized element (e.g., ionic iron), a therapeutic, a bioactive-agent, and the like. In various embodiments described herein, the active agent 35 comprises ionic iron.

Embodiments of a system 90 for transdermal iontophoretic delivery can comprise patch 10i including active electrode assembly 60 and a return electrode assembly 70 as well as a power supply 80 as is shown in the embodiments of FIG. 12. Return electrode assembly 70 includes a connector 71 and electrode 72 and can positioned on a second patch 10' or the same patch 10i. Active electrode assembly 60 and return electrode assembly 70 are coupled to opposite poles or terminals 81 of an electrical power source 80, for example, a chemical battery or an external power station connected to the iontophoresis device via electrical leads. As described above, each electrode assembly 60 includes an electrode element (or electrode) 62 to apply an electromotive force and/or current to reservoir 12 and/or delivery layer 20. The active agent 35 may be either cationic or anionic, and the power source 80 may be configured to apply the appropriate voltage and polarity based on the polarity of the active agent. Iontophoresis may be advantageously used to enhance or control the delivery rate of the active agent. In various embodiments, the active agent 35 can be stored in a reservoir 12 which in particular embodiments can comprise a cavity. See e.g., U.S. Pat. No. 5,395, 310. Alternatively, the active agent may be stored in a reservoir such as a porous structure or a gel. An ion exchange membrane may be positioned to serve as a polarity selective barrier between the active agent reservoir and the biological interface. The membrane, typically only permeable with respect to one particular type of ion (e.g., a charged active agent), prevents the back flux of oppositely charged ions from the skin or mucous membrane. Further illustrations of the use of iontophoresis in the transdermal delivery of pharmaceutical compositions is described in U. S. Patent Application Publication Nos.: 2007/0093799, 2007/0088243, 2007/0083186, 2007/0083185, and 2007/0083151, each of which is incorporated by reference herein in its entirety.

Particular embodiments of the invention provide transdermal patches configured to actively deliver pharmaceutical compositions comprising at least one iron-containing compound to an individual in need thereof. Active modes of delivery include, but are not limited to thermophoresis, iontophoresis, magnetophoresis, and sonophoresis. Accordingly, in various embodiments, pharmaceutical compositions of the present invention can be actively delivered to an individual in need thereof by an active delivery selected from the group consisting of thermophoresis, iontophoresis, magnetophoresis, and sonophoresis.

As described above, iontophoresis involves the delivery of charged chemical compounds across the skin membrane using an applied electrical field. see e.g. "Pharmaceutical Dosage Forms and Drug Delivery Systems—Chapter 10—Transdermal Drug Delivery Systems, Ointments, Creams, Lotions and Other Preparations", ed. by Ansel et al., Williams & Wilkins, page 360, (1995). Magnetophoresis involves the use of a magnetic field to enhance drug delivery to the skin. see e.g. Murthy et al., "Physical and Chemical Permeation Enhancers in Transdermal Delivery of Terbutaline Sulphate", AAPS Pharm Sci Tech. 2001; 2(1). Sonophoresis is the use of high-frequency ultrasound which serves to compromise the integrity of the stratum corneum layer and improve permeability of compounds through the skin.

Iron-Containing Compounds of the Present Invention

The present invention contemplates, in part, a method for the administration of a therapeutically effective amount of elemental iron, including, but not limited to administration of ionic irons. A therapeutically effective amount of ionic iron, present in an embodiment of a pharmaceutical composition of the present invention can be in the form of one or more iron-containing compounds, such as soluble ferrous salts, but may further include, without limitation, slightly soluble ferrous salts, insoluble ferrous salts, carbonyl irons, and blends, mixtures or combinations thereof.

Accordingly, in preferred embodiments, the invention provides methods and/or delivery vehicles such as one or more transdermal patches described herein, for the administration of selected soluble ferrous salt(s) including, without limitation, ferrous sucrose, ferrous sulfate, ferrous gluconate, ferrous fumarate, ferric hypophosphite, ferric albuminate, ferric chloride, ferric citrate, ferric oxide saccharated, ferric ammonium citrate, ferrous chloride, ferrous iodide, ferrous lactate, ferric trisglycinate, ferrous bisglycinate, ferric nitrate, ferrous hydroxide saccharate, ferric sulfate, ferric gluconate, ferric aspartate, ferrous sulfate heptahydrate, ferrous phosphate, ferric ascorbate, ferrous formate, ferrous acetate, ferrous malate, ferrous glutamate, ferrous cholinisocitrate, ferroglycine sulfate, ferric oxide hydrate, ferric pyrophosphate soluble, ferric hydroxide saccharate, ferric manganese saccharate, ferric subsulfate, ferric ammonium sulfate, ferrous ammonium sulfate, ferric sesquichloride, ferric choline citrate, ferric manganese citrate, ferric quinine citrate, ferric sodium citrate, ferric sodium edetate, ferric formate, ferric ammonium oxalate, ferric potassium oxalate, ferric sodium oxalate, ferric peptonate, ferric manganese peptonate, other pharmaceutically acceptable soluble ferrous salts, blends, mixtures and/or combinations thereof.

In particular embodiments, methods and/or delivery vehicles of the present invention comprise the administration of selected soluble ferrous salt(s), optionally in conjunction therewith, a slightly soluble salt(s) may be utilized in the compositions of the present invention, wherein the slightly soluble salt(s) may include, without limitation, ferric acetate, ferric fluoride, ferric phosphate, ferric pyrophosphate, ferrous pyrophosphate, ferrous carbonate saccharated, ferrous carbonate mass, ferrous succinate, ferrous citrate, ferrous tartrate, ferric fumarate, ferric succinate, ferrous hydroxide, ferrous nitrate, ferrous carbonate, ferric sodium pyrophosphate, ferric tartrate, ferric potassium tartrate, ferric subcarbonate, ferric glycerophosphate, ferric saccharate, ferric hydroxide saccharate, ferric manganese saccharate, ferrous ammonium sulfate, other pharmaceutically acceptable slightly soluble ferrous salts, blends, mixtures and/or combinations thereof.

In certain particular embodiments, methods and/or delivery vehicles of the present invention provide for the administration of pharmaceutical compositions comprising selected soluble iron salt(s) and/or slightly soluble salt(s), or in conjunction therewith, an insoluble salt(s), wherein the insoluble salt(s) may include, without limitation, ferric sodium pyrophosphate, ferrous carbonate, ferric hydroxide, ferrous oxide, ferric oxyhydroxide, ferrous oxalate, other pharmaceutically acceptable insoluble ferrous salts, blends, mixtures and/or combinations thereof.

One having ordinary skill in the art would recognize that any of the foregoing ferrous salts in any combination and concentration may be selected and adjusted on the basis of a variety of treatment parameters, including, by way of non-limiting example, the characteristics of the patient, the iron deficiency being treated, and the therapeutic outcome desired, all of which may be discerned by methods well known in the art.

In one embodiment, any one or more of the foregoing enumerated ferrous salts, or in conjunction therewith, the compositions of the present invention may selectively comprise a chelated iron in combination with the selected heme iron and/or heme iron polypeptide. Accordingly, in such an embodiment, the chelated iron of the present composition may be selected from any one or more of the preferred complexes of iron polysaccharide, iron bis glycinate, and/or iron proteinate. However, alternate chelated iron complexes are contemplated and, as such, may include, without limitation, methylidine-iron complex, EDTA-iron complex, phenanthrolene iron complex, p-toluidine iron complex, ferrous saccharate complex, ferrlecit, ferrous gluconate complex, ferrum vitis, ferrous hydroxide saccharate complex, iron-arene sandwich complexes, acetylacetone iron complex salt, iron-dextran complex, iron-dextrin complex, iron-sorbitol-citric acid complex, saccharated iron oxide, ferrous fumarate complex, iron porphyrin complex, iron phtalocyamine complex, iron cyclam complex, dithiocarboxy-iron complex, desferrioxamine-iron complex, bleomycin-iron complex, ferrozine-iron complex, iron perhaloporphyrin complex, alkylenediamine-N,N'-disuccinic acid iron(III) complex, hydroxypyridone-iron(III) complex, aminoglycoside-iron complex, transferrin-iron complex, iron thiocyanate complex, iron complex cyanides, porphyrinato iron(III) complex, polyaminopolycarbonate iron complexes, dithiocarbamate iron complex, adriamycin iron complex, anthracycline-iron complex, MGD-iron complex, ferrioxamine B, ferrous citrate complex, ferrous sulfate complex, ferric gluconate complex, ferrous succinate complex, polyglucopyranosyl iron complex, polyaminodisuccinic acid iron complex, biliverdin-iron complex, deferiprone iron complex, ferric oxyhydride-dextran complex, dinitrosyl dithiolato iron complex, iron lactoferrin complexes, 1,3-PDTA ferric complex salts, diethylenetriaminepentaacetic acid iron complex salts, cyclohexanediaminetetraacetic acid iron complex salts, methyliminodiacetic acid iron complex salts, glycol ether diaminetetraacetic acid iron complex salts, ferric hydroxypyrone complexes, ferric succinate complex, ferric chloride complex, ferric glycine sulfate complex, ferric aspartate complex, sodium ferrous gluconate complex, ferrous hydroxide polymaltose complex, other pharmaceutically acceptable chelated iron complexes, blends, mixtures and/or combinations thereof.

In particular embodiments, the present invention provides for a pharmaceutical composition comprising at least one, at least two, at least three, at least four, at least five, at least six, at least seven, at least eight, at least nine, at least ten or more ferrous salts, or blends, mixtures and/or combinations thereof.

In other embodiments, the present invention provides for a pharmaceutical composition comprising one or more, two or more, three or more, four or more, five or more, six or more, seven or more, eight or more, nine or more, ten or more, or any number of ferrous salts, or blends, mixtures and/or combinations thereof.

Other embodiments of the invention provide for a pharmaceutical composition which can comprise one, two, three, four, five, six, seven, eight, nine, ten, or more ferrous salts, or blends, mixtures and/or combinations thereof. Still additional numbers of salts are also contemplated.

In a preferred embodiment, a therapeutically effective amount of iron is delivered in the form of one or more ferrous salts selected from the group consisting of ferrous sucrose, ferrous gluconate, ferrous chloride, ferrous sulfate, and ferrous fumarate.

In further embodiments, pharmaceutical compositions of the present invention comprise one or more iron-containing compounds and one or more vitamin supplements.

Vitamin Supplements

In particular embodiments, the iron-containing compositions (e.g., compositions comprising ferrous salts) of the present invention may further selectively comprise one or more or particular vitamin supplements and/or minerals, including, without limitation, folic acid, vitamin A, vitamin B (all series, including B3, B6, B12), vitamin C, vitamin D, vitamin E, vitamin K, calcium, magnesium, or the like, in order facilitate treatment of an iron deficiency as described herein. As used herein, the term "vitamin C" means any form of vitamin C, including ascorbate and L threonate. As used herein, the term "vitamin D" means both cholecalciferol (vitamin D3) and ergocalciferol (vitamin D2). As used herein, the term "vitamin E" means alpha-tocopherol, D-alpha-tocopherol, D-alpha-tocopheryl succinate (or acetate), DL-alpha-tocopherol, DL-alpha-tocopheryl acetate (or succinate), gamma tocopherol, mixed tocopherols, and DL-alpha tocopherol nicotinate. As used herein, the term "calcium" means any form of calcium including calcium carbonate, phosphate, lactate, gluconate, citrate and combinations thereof. As used herein, the term "magnesium" means any form of magnesium, including magnesium oxide, magnesium chloride, magnesium lactate, magnesium sulfate and magnesium gluconate.

In particular embodiments, the present invention also provides for the administration of an iron containing composition comprising one or more ferrous salts in combination with one or more vitamin supplements, wherein the vitamin supplements comprise one or more B vitamins.

The B vitamins are water-soluble. The B vitamins included in the multi-vitamin and mineral supplement are thiamin (vitamin B1), riboflavin (vitamin B2), niacin (vitamin B3), pantothenic acid (vitamin B5), pyridoxine (vitamin B6), biotin, folic acid, the cobalamins (vitamin B12), and choline. Vitamin B1 or thiamin helps keep collagen-rich connective and mucous membranes healthy, helps to maintain smooth muscles, helps in the formation of blood cells, and is necessary for proper nervous system function. Vitamin B2 or riboflavin is necessary for healthy hair, nails, and mucous membranes and is involved in red blood cell formation, antibody production, and overall growth. Vitamin B3 or niacin helps in the production of most of the sex hormones, dilates blood vessels, lowers cholesterol, and helps maintain blood circulation. Niacin is the generic name for a group of compounds which exhibit niacin activity, and includes niacinamide and nicotinic acid. Vitamin B6 or pyridoxine is involved in the production of ribonucleic acid (RNA) and deoxyribonucleic acid (DNA) and many other reactions in the body. Pyridoxine refers to and includes three different compounds: pyridoxine, pyridoxamine, and pyridoxal. Folic acid is essential in the production of red blood cells, the production of hormones, and the synthesis of DNA. Vitamin B12 or the cobalamins is necessary for overall metabolism, the function of the nervous system, metabolism of folic acid, and the production of red blood cells. There are at least three active forms of cobalamin: cyanocobalamin, hydroxocobalamin, and nitrocobalamin. Biotin is necessary for the metabolism of carbohydrates, proteins, and fats and is needed for healthy skin and hair. Pantothenic acid is important for the production of adrenal gland hormones, increases overall energy, and helps convert food into energy. Choline is necessary for nervous system function and brain function. It is also important for gall bladder and liver function.

The various compositions of the present invention may include one or more forms of the foregoing vitamins and/or minerals in any amount and in any combination with a selected ferrous salt(s) and/or other iron-containing compound as described elsewhere herein. In preferred embodiments, compositions of the present invention comprising a therapeutically effective amount of iron from one or more iron-containing compounds (e.g., ferrous salts), further comprise one or more vitamin supplements. In particular preferred embodiments, compositions of the present invention comprising a therapeutically effective amount of iron from one or more iron-containing compounds (e.g., ferrous salts), further comprise one or more vitamin supplements selected from the group consisting of thiamine, riboflavin, niacin, pantothenic acid, pyroxidine, biotin, folic acid, colbalamin, and choline.

One having ordinary skill in the art, would recognize that suitable doses of a vitamin supplements in an iron-containing composition of the present invention can be determined by routine methods well known to those in the art, and described in, for example, Goodman & Gilman's "The Pharmacological Basis of Therapeutics, Eleventh Edition. McGraw-Hill, 2005", "Remington: The Science and Practice of Pharmacy, 20th Edition. Baltimore, Md.: Lippincott Williams & Wilkins, 2000.", and "The Merck Index, Fourteenth Edition. Whitehouse Station, N.J.: Merck Research Laboratories, 2006", incorporated herein by reference in relevant parts.

In further embodiments, pharmaceutical compositions of the present invention can comprise one or more iron-containing compounds, one or more vitamin supplements, and one or more erythropoietin stimulating agents. An erythropoietin stimulating agent is a recombinant form of erythropoietin, or a derivative thereof, that stimulates the production of red blood cells in bone marrow and is useful in the treatment for iron deficiency. Examples of erythropoietin stimulating agents include erythropoietin, epoetin (e.g., Procrit, Epogen, and Eprex), darbepoetin (Aranesp), and PDpoietin (an erythropoietin produced in Iran by Pooyesh Darou Pharmaceuticals).

Thus, in one embodiment, a composition comprising a therapeutically effective amount of iron from one or more iron-containing compounds, one or more vitamin supplements, erythropoietin, and one or more erythropoietin stimulating agents is transdermally administered to an individual in need thereof.

Pharmaceutically Acceptable Carriers

In particular embodiments, the iron-containing compositions (e.g., compositions comprising ferrous salts) of the present invention may further selectively comprise one or more or pharmaceutically acceptable carriers. In one aspect, the pharmaceutically acceptable carrier can be an ointment including an iron-containing compound. An ointment is a semisolid pharmaceutical preparation based on well known materials such as oleaginous bases, lanolins, emulsions, or water-soluble bases. Preparation of ointments is well known in the art such as described in Remington: The Science and Practice of Pharmacy 19th ed. (1995), vol. 2, pp. 1585-1591, which is incorporated herein by reference. Such preparations often contain petrolatum or zinc oxide. Oleaginous ointment bases suitable for use in the present invention include generally, but are not limited to, vegetable oils, animal fats, and semisolid hydrocarbons obtained from petroleum. Absorbent ointment bases of the present invention may contain little or no water and may include components such as, but not limited to, hydroxystearin sulfate, anhydrous lanolin and hydrophilic petrolatum. Emulsion ointment bases of the present invention are either water-in-oil (W/O) emulsions or oil-in-water (O/W) emulsions, and may include, but are not limited to, cetyl alcohol, glyceryl monostearate, lanolin, polyalkylsiloxanes, and stearic acid. Water-soluble ointment bases suitable for use in the present invention may be prepared from polyethylene glycols of varying molecular weight.

In another embodiment of the present invention, the pharmaceutically acceptable carrier can be a cream including an iron-containing compound. Creams are a type of ointment which are viscous liquids or semisolid emulsions, either oil-in-water or water-in-oil, as is well known in the art. Cream bases may be soluble in water, and contain an oil phase, an emulsifier, an aqueous phase, and the active agent. In a detailed aspect of the present invention, the oil phase may be comprised of petrolatum and a fatty alcohol such as cetyl or stearyl alcohol. In another detailed aspect of the present invention, the aqueous phase may exceed the oil phase in volume, and may contain a humectant. In another embodiment of the present invention, the emulsifier in a cream formulation may be a nonionic, anionic, cationic or amphoteric surfactant.

In another embodiment of the present invention, the pharmaceutically acceptable carrier can be a lotion including an iron-containing compound. A lotion is an ointment which may be a liquid or semi-liquid preparation in which solid particles, including the active agent, are present in a water or alcohol base. Lotions suitable for use in the present invention may be a suspension of solids or may be an oil-in-water emulsion. In another aspect of the present invention, lotions may also contain suspending agents which improve dispersions or other compounds which improve contact of the active agent with the skin, e.g., methylcellulose, sodium carboxymethylcellulose, or similar compounds.

In yet another embodiment of the present invention, a pharmaceutically acceptable carrier can be a paste including an iron-containing compound. Pastes of the present invention are ointments in which there are significant amounts of solids which form a semisolid formulation in which the active agent is suspended in a suitable base. In a detailed aspect of the present invention, pastes may be formed of bases to produce fatty pastes or made from a single-phase aqueous gel. Fatty pastes suitable for use in the present invention may be formed of a base such as petrolatum, hydrophilic petrolatum or the like. Pastes made from single-phase aqueous gels suitable for use in the present invention may incorporate cellulose based polymers such as carboxymethylcellulose or the like as a base.

In another embodiment of the present invention, a pharmaceutically acceptable gel may be prepared that includes an iron-containing compound. A gel prepared in accordance with the present invention may be a preparation of a colloid in which a disperse phase has combined with a continuous phase to produce a viscous product. The gelling agent may form submicroscopic crystalline particle groups that retain the solvent in the interstices. As will be appreciated by those working in art, gels are semisolid, suspension-type systems. Single-phase gels can contain organic macromolecules distributed substantially uniformly throughout a carrier liquid, which may be aqueous or non-aqueous and may contain an alcohol or oil.

In addition to containing an iron-containing compound, the pharmaceutically acceptable carriers of the transdermal formulations recited herein, may include a number of other additives, such as vitamin supplements, erythropoietin, erythropoietin stimulating agents, cyclodextrins, diluents, transdermal permeabilization agents, excipients, emollients, plasticizers, skin irritation reducing agents, stabilizing compounds, or any mixtures or combinations thereof. These types of components, as well as others not specifically recited, are well known in the art for inclusion in various transdermal formulations (e.g., pharmaceutical compositions of the present invention), and may be added as desired to the transdermal drug delivery system of the present invention in specific types and amounts in order to achieve a desired result.

Transdermal Permeabilizing Agents

In particular embodiments, the iron-containing compositions (e.g., compositions comprising ferrous salts) of the present invention may further selectively comprise one or more or particular transdermal permeabilizing agents in order to increase the permeability of the skin to the iron-containing compound(s). For example, useful penetration enhancers may include, without limitation, fatty acids, fatty acid esters, fatty alcohols, fatty acid esters of lactic acid or glycolic acid, glycerol tri-, di-, and monoesters, triacetin, short chain alcohols, and mixtures thereof. In one specific aspect, the penetration enhancer may include lauryl alcohol, isopropyl myristate, or a combination of lauryl alcohol and isopropyl myristate. In other aspects, specific species or combinations of species may be selected from the above listed classes of compounds by one skilled in the art, in order to optimize enhancement of the particular atomoxetine compound employed.

Further examples of suitable skin penetration enhancers include sulfoxides, alcohols, fatty acids, fatty acid esters, polyols, amides, surfactants, terpenes, alkanones, and organic acids, among others. Specific examples of suitable sulfoxides include dimethylsulfoxide (DMSO) and decylmethylsulfoxide, among others. Suitable alcohols include alkanols such as ethanol, propanol, butanol, pentanol, hexanol, octanol, n-octanol, nonanol, decanol, 2-butanol, 2-pentanol, and benzyl alcohol; fatty alcohols, such as caprylic alcohol, decyl alcohol, lauryl alcohol, 2-lauryl alcohol, myristyl alcohol, cetyl alcohol, stearyl alcohol, oleyl alcohol, linoleyl alcohol, and linolenyl alcohol; and isopropyl alcohol. Examples of suitable fatty acids include linear fatty acids such as valeric acid, heptanoic acid, pelagonic acid, caproic acid, capric acid, lauric acid, myristic acid, stearic acid, oleic acid, and caprylic acid; and branched fatty acids, such as isovaleric acid, neopentanoic acid, neoheptanoic acid, neononanoic acid, trimethyl hexanoic acid, neodecanoic acid, and isostearic acid.

Examples of suitable fatty acid esters include aliphatic fatty acid esters such as isopropyl n-butyrate, isopropyl n-hexanoate, isopropyl n-decanoate, isopropyl myristate, isopropyl palmitate, and octyldodecyl myristate; alkyl fatty acid esters such as ethyl acetate, butyl acetate, methyl acetate, methylvalerate, methylpropionate, diethyl sebacate, and ethyl oleate; and diisopropyl adipate and dimethyl isosorbide.

Examples of suitable polyols include propylene glycol, butylene glycol, polyethylene glycol, ethylene glycol, diethylene glycol, triethylene glycol, dipropylene glycol, ethoxydiglycol, pentylene glycol, glycerol, propanediol, butanediol, pentanediol, hexanetriol, and glycerin.

Examples of suitable amides include urea, dimethylacetamide, diethyltoluamide, dimethylformamide (DMF), dimethyloctamide, dimethyldecamide, biodegradable cyclic urea (e.g., 1-alkyl-4-imidazoline-2-one), pyrrolidone derivatives, biodegradable pyrrolidone derivatives (e.g., fatty acid esters of N-(2-hydroxyethyl)-2-pyrrolidone), cyclic amides, hexamethylenelauramide and its derivatives, diethanolamine, and triethanolamine. Examples of pyrrolidone derivatives include 1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl-4-methoxycarbonyl-2-pyrrolidone, 1-lauryl-4-methoxycarbonyl-2-pyrrolidone, N-cyclohexylpyrrolidone, N-dimethylaminopropylpyrrolidone, N-cocoalkypyrrolidone, N-tallowalkylpyrrolidone, and N-methylpyrrolidone.

Examples of cyclic amides include 1-dodecylazacycloheptane-2-one (e.g., Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11-trimethyldodecyl)azacyclohaptane-2-one, 1-geranylazacyclohexane-2-one, 1-geranylazacyclopentan-2,5-dione, and 1-farnesylazacyclopentan-2-one.

Suitable surfactants may include anionic surfactants, cationic surfactants, nonionic surfactants, bile salts, and lecithin. Examples of suitable anionic surfactants include sodium laurate, sodium lauryl sulfate, and sodium laureth sulfate. Suitable cationic surfactants include cetyltrimethyl ammonium bromide, tetradecyltrimethylammonium bromide, benzalkonium chloride, octadecyltrimethylammonium chloride, cethylpyridinium chloride, dodecyltrimethylammonium chloride, and hexadecyultrimethylammonium chloride. Examples of suitable nonionic surfactants include poloxamer 231, poloxamer 182, poloxamer 184, Brij® 30 (polyoxyethylene (4) lauryl ether), Brij® 93 (polyoxyethylene (2) oleyl ether), Brij® 96 (polyoxyethylene (20) oleyl ether), Brij® 99 (polyoxyl (10) oleyl ether), Span® 20 (sorbitan monolaurate), Span® 40 (sorbitane monopalmitate), Span®60 (sorbitane monostearate), Span® 80 (sorbitane monooleate), Span® 85 (sorbitane trioleate), TWEEN® 20 (polyethylene glycol sorbitan monolaurate; polyoxyethylene (20) sorbitan monolaurate), TWEEN® 40 (polyoxyethylene (20) sorbitan monopalmitate), TWEEN® 60 (polyethylene glycol sorbitan monostearate; polyoxyethylene (20) sorbitan monostearate), TWEEN® 80 (polyethylene glycol sorbitan monooleate; polyoxyethylene (20) sorbitan monooleate), Myrj® 45 (polyoxyethylene (8) stearate), Myrj® 51 (polyoxyethylene stearate), Myrj® 52 (polyoxyethylene stearate), and Miglyol 840 (propylene glycol dicaprylate/dicaprat), among others. Examples of suitable bile salts include sodium cholate, and sodium salts of taurocholic, glycholic, and desoxycholic acids.

Suitable terpenes include hydrocarbons (e.g., D-limonene, α-pinene, β-carene, etc.), alcohols (e.g. α-terpineol, terpinen-4-ol, carvol, etc.), ketones (e.g., carvone, pulegone, piperitone, menthone, etc.), oxides (e.g., cyclohexene oxide, limonene oxide, α-pinene oxide, cyclopentene oxide, 1,8-cineole, etc.), and oils (e.g., ylang ylang, anise, chenopodium, eucalyptus, peppermint, etc.). Examples of suitable alkanones include N-heptane, N-octane, N-nonane, N-decane, N-undecane, N-dodecane, N-tridecane, N-tetradecane, and N-hexadecane, among others. Examples of suitable organic acids include salicylic acid and salicylates (including their methyl, ethyl, and propyl glycol derivatives), citric acid, and succinic acid, among others.

Other examples of suitable transdermal permeabilizing agents are known in the art and include, for example, monoglycerides, polyglycosylated glycerides, glyceryl monoethyl ether, polysorbates, beta-cyclodextrin, cyclopentadecalactone, alkyl-2-(N,N-disubstituted amino)-alkanoate ester, 2-(n-nonyl)-1,3-dioxolane, isopropyl myristate, terpinol, menthol, cineol, monoolein, sodium oleate, oleyl oleate, laurylcapram, bisabolol, capaicin, and capsicum. Other examples of suitable skin penetration enhancers and a description of their mechanism of action may be found in Goodman and Barry, "Percutaneous Absorption," in Mechanisms-Methodology-Drug Delivery, 2nd Edition, Bronaugh and Maibach, eds., 1989, pp. 567-593, Marcel Dekker, Inc., N.Y.

In a particular embodiment, the transdermal permeabilizing agent is selected from the group consisting of n-octanol, D-limonene, oleic acid, cineol, isopropyl myristate, monooleate, monoolein, sodium oleate, oleyl oleate, laurylcapram, sodium lauryl sulfate, bisabolol, DMSO, ethanol, propanol, benzyl alcohol, lauryl alcohol, lauric acid, myristic acid, isopropyl palmitate, diisopropyl adipate, dimethyl isosorbide, propylene glycol, butylene glycol, polyethylene glycol, dipropylene glycol, ethoxydiglycol, pentylene glycol, urea, lecithin, sodium laureth sulfate, benzalkonium chloride, poloxamer 231, Brij® 30, Span® 20, Tween® 20, oil (e.g., ylang ylang, eucalyptus, peppermint), salicylic acid, citric acid, menthol, capaicin, capsicum, and combinations thereof.

In another particular embodiment, the transdermal permeabilizing agent is selected from the group consisting of oleic acid, laurocapram, sodium lauryl sulphate, bisabolol, DMSO, ethanol, lauric acid, myristic acid, isopropyl myristate, isopropyl palmitate, diisopropyl adipate, dimethyl isosorbide, propylene glycol, butylene glycol, polyethylene glycol, dipropylene glycol, ethoxydiglycol, pentylene glycol, lecithin, benzalkonium chloride, D-limonone, oil (e.g., ylang ylang, eucalyptus, peppermint), salicylic acid, menthol, capaicin, capsicum, and combinations thereof.

Cyclodextrins

Pharmaceutical compositions of the present invention comprise a therapeutically effective amount of iron from one or more iron-containing compounds, and/or one or more compounds or agents selected from the group consisting of vitamin supplements, erythropoietin stimulating agents, erythropoietin, pharmaceutically acceptable carriers, transdermal permeabilizing agents, and cyclodextrins. As used herein and in the claims, the term "cyclodextrin" refers to any of a family of cyclic oligosaccharides. Cyclodextrins, also sometimes called cycloamyloses, are composed of, but are not necessarily limited to, five or more D-glucopyranoside units, connected by α-(1,4) glycosidic linkages, as in amylose. Cyclodextrins having as many as 32 1,4-glucopyranoside units have been well characterized. Cyclic oligosaccharides as large as 150 units have been identified. Typically, cyclodextrins contain, but are not necessarily limited to, six to eight glucopyranoside units in a ring, commonly termed α-cyclodextrin (six units), β-cyclodextrin (seven units), and gamma-cyclodextrin (eight units). These may be naturally occurring or produced synthetically. Cyclodextrins may be produced from starch by use of readily available enzymes, for example, α-amylase and cyclodextrin glycosyltransferase (CGTase), an enzyme that is produced by a number of different organisms. In certain methods known in the art, for example, starch may first be either heated or treated with α-amylase, followed by enzymatic conversion with CGTase. The conversion typically yields a mixture of the three common cyclodextrins, the ratio of which depends on the particular CGTase employed in the conversion reaction. The characteristic solubility of each of the three cyclodextrins in water is utilized in purification schemes. β-Cyclodextrin, for example, is poorly soluble in water, and may be isolated by crystallization. α- and γ-Cyclodextrins, which are much more water-soluble, may be purified chromatographically. Alternatively, synthetic methods utilizing certain organic agents may preferentially drive the reaction toward the formation of a specific cyclodextrin, by complexing with the specific cyclodextrin and causing it to precipitate from the reaction mixture as the conversion reaction proceeds. The specific cyclodextrin can then be isolated by recovery of the precipitate and separation from the agent used to form the complex.

The most stable three-dimensional configuration of a cyclodextrin is represented topologically as a toroid, wherein the smaller and the larger openings of the toroid expose primary and secondary hydroxyl groups, respectively, to the aqueous environment into which the cyclodextrin is placed. These regions are considerably less hydrophilic than the aqueous environment. The interior of the toroid is hydrophobic. The exterior of the toroidal cyclodextrin is sufficiently hydrophilic to allow it to dissolve in water.

Cyclodextrins are used in a broad range of applications in the pharmaceutical, food, and chemical industries. Cyclodextrins can act as transdermal permeabilizing agents as well as to increase the solubility of compounds. Complexes with a variety of chemical substances may be formed in the apolar interior environment of the cyclodextrin cavity, resulting from a combination of van der Waals forces, hydrogen bonding, and hydrophobic interactions. Inclusion of a compound in the interior of a cyclodextrin may greatly modify the physical and/or chemical properties of that compound in solution. For example, inclusion of a poorly soluble component of a pharmaceutical composition within a cyclodextrin may enable such an agent to penetrate biological interfaces or body tissues by virtue of its increased compatibility with the aqueous environment. Having passed through a biological interface and/or into a body tissue, the decrease in concentration of the cyclodextrin complex in the aqueous environment may lead to spontaneous dissociation of the cyclodextrin, releasing the components of the composition into the tissue.

Iron Deficiency

Iron deficiency is one of the most common nutritional deficiencies worldwide and is the leading cause of anemia on a global basis. Iron balance is fundamentally regulated by the rate of erythropoiesis and the size of iron stores. Iron deficiency can occur with or without anemia, and has been associated with growth defects and impaired cognitive development, especially in neonates and children. Research in Chile has shown that 40 percent of children whose main source of nutrition was breast milk developed iron-deficiency anemia. Such children can appear tired and inattentive, and they can suffer from delayed motor development. Some children or neonates can even develop mild to moderate mental retardation as a result of iron-deficiency anemia. The association between iron deficiency anemia and diminished mental, motor, and behavioral development in infants is not a recent discovery. A possible link was noted in the late 1970s, and subsequent studies of 12- to 23-month-old infants in the past two decades confirmed those findings. By the 1990s, the association between iron deficiency anemia and lower developmental test scores was well-established but may not have received the expected amount of attention in the United States because of the shrinking prevalence of iron deficiency anemia. In recent years, it has become clear that these effects are long-lasting despite correction of the iron deficiency anemia.

Mental, motor, and behavior effects develop only when iron deficiency is severe enough to cause anemia. In studies using Bayley Scales of Infant Development, infants with iron deficiency anemia receive lower scores on mental and motor tests, including gross and fine motor coordination, and demonstrate affective differences, such as wariness, fearfulness, and unhappiness. These findings have been confirmed by a variety of studies in different cultural settings. Further study of the behavior component found activity differences, with the anemic infants being less playful, tiring more easily, and preferring to be held. These mental and motor effects are not detectable on routine physical examination; it is not known if the behavior changes are noticeable.

Iron deficiency can be defined as inadequate iron supply (levels or stores) or as inadequate availability or utilization of iron in the body. This can be due to nutritional deficiencies, e.g., lack of iron in the diet; to iron malabsorption, due, for example, to surgery (post-gastrectomy) or disease (Crohn's disease); or to a depletion in iron supply or increased iron loss due to chronic or acute blood loss resulting from injury or trauma, chemotherapy, colon cancer, menses, blood donation, phlebotomy (such as due to various procedures, surgeries); from increased iron demand, e.g., due to rapid growth in infancy or adolescence, pregnancy, erythropoietin therapy, etc. Infants and toddlers aged 6 to 24 months are particularly vulnerable to developing iron deficiency. They have a rapid rate of growth and blood volume expansion and the need for exogenous iron is high in proportion to body weight.

Iron deficiency may also include functional iron deficiency, e.g., iron deficiency characterized by the subject's impaired ability to access and utilize iron stores. Iron is not available at a rate sufficient to allow normal hemoglobinization of erythrocytes, leading to reduced reticulocyte and erythrocyte cellular hemoglobin content. Functional iron deficiency is often seen in healthy individuals with apparently normal or even increased iron stores but with impaired iron availability, as measured, e.g., by low levels of percent transferrin saturation. This type of iron deficiency is frequently associated with acute or with chronic inflammation.

Iron deficiency of any kind can lead to iron-deficient or iron-restricted erythropoiesis, in which red blood cell numbers decrease and circulating red blood cells are smaller than normal (microcytic) and lack adequate hemoglobin, and as such are pale in color (hypochromic).

One having ordinary skill in the art is acutely aware of the metabolic indicators of iron deficiency in various different populations, e.g., athletes, pregnant women, adolescents, and neonates. For example, individuals having functional iron deficiency, can develop impaired hemoglobin synthesis, reduced % transferrin saturation, and decreased hemoglobin and hematocrit levels, leading to iron deficiency anemia. A soluble form of ferritin is released into circulation during ferritin synthesis. The amount of ferritin in the circulation (measured as serum ferritin) has been shown to correlate with total body iron stores. For example, an indicator of absolute iron deficiency is defined as serum ferritin levels less than about 100 ng/mL and TSAT levels less than about 20%. Transferrin saturation represents the amount of protein-bound iron in circulation, i.e., the amount readily available for erythropoiesis. Transferrin saturation is calculated by dividing serum iron by total iron-binding capacity (TIBC) and then multiplying the result by 100. Total iron-binding capacity is a measure of the total binding capacity of transferrin. Normal TSAT is about 30% to about 50%. A TSAT value less than about 20% indicates iron deficiency, while a level of about 50% or greater indicates iron overload. A hematocrit (HCT) of less than about 33% and/or a hemoglobin saturation (Hb) of less than about 11 g/dL in premenopausal women and patients before puberty indicates iron deficiency. A HCT of less than about 37% and/or Hb of less than about 12 g/dL in adult males and postmenopausal females indicates iron deficiency.

Iron deficiency anemia is the most common anemia in the world. Iron is an essential component of hemoglobin; without iron, the marrow is unable to produce hemoglobin effectively. Iron deficiency anemia may occur in subjects with depleted or impaired iron supply, or may occur in subjects having functional iron deficiency, when iron is present in storage but is unavailable, e.g., for hemoglobin production.

Iron metabolism encompasses in general the processes by which a cell, tissue, organ, organ system, or whole organism maintains iron homeostasis by altering, e.g., increasing or decreasing, specific processes of iron metabolism. Iron metabolism or iron metabolic processes encompass processes involving iron processing, transport, uptake, utilization, storage, mobilization, absorption, etc. Specific aspects of iron metabolism and processing include expression of iron transporters and enzymes which facilitate movement of iron across a cell membrane and retention or secretion of iron by a cell; alteration in expression of proteins involved in iron transport in blood; alteration in expression of transferrin and transferrin receptors; alteration in expression and/or activity of proteins involved in iron absorption; alteration in expression and activity of iron associated transcriptional and translational regulatory proteins; and alteration of iron distribution within body or culture fluids, including, e.g., interstitial (i.e., extracellular), intracellular, blood, bone marrow, and the like.

Many embodiments of the invention provide a method for treating and/or preventing an iron deficiency in an individual comprising: i) contacting the skin or other portion of the individual with a transdermal patch of the present invention, which comprises a composition comprising a therapeutically effective amount of iron from at least one iron-containing compound as described herein; and ii) delivering a therapeutically effective amount of iron to the individual, thereby preventing and/or treating an iron deficiency in an individual.

In various embodiments, the individual being treated may be a neonate, an infant, a child, an adolescent, a pre-menopausal woman, a post-menopausal woman, a pregnant woman, a man or an athlete. In particular embodiments, the individual being treated can have an iron deficiency without anemia. In other particular embodiments, an individual is being treated to prevent iron deficiencies associated with growth retardation and cognitive disabilities and/or mental retardation. In related embodiments, the individual being treated is a neonate, infant, or pregnant woman.

In other particular embodiments, an individual being treated may have an iron deficiency caused by chronic alcoholism; poor nutrition; decreased consumption of animal protein and absorbic acid; increased iron demands of pregnancy, infancy, or adolescence; malabsorption syndromes; and foods or drugs that reduce the gastrointestinal absorption of iron.

In particular embodiments, the individual being treated may have an iron deficiency anemia. In other particular embodiments, an individual being treated may have an iron deficiency caused by one or more of drugs, peptic ulcer disease, hemorrhoids, trauma, surgery, gastrointestinal bleeding, dialysis, pulmonary bleeding, uterine bleeding, menstruation, birth, urinary tract bleeding, and blood donation; primary achlorhydia, secondary achlorhydia secondary to use of compounds that reduce stomach acid pH; gastrointestinal disease; Crohn's disease; ulcerative colitis; sprue; gastric bypass surgery; pernicious anemia; intestinal parasites; hookworm infection; trichuriasis; functional iron deficiency resulting from the use of erythropoietic stimulating agents; inflammatory diseases autoimmune diseases; renal failure; cancer; and beta thalassemia.

In other particular embodiments, an individual being treated may have an iron deficiency characterized by microcytosis of red blood cells, a hemoglobin iron binding capacity of less than 20%, ferritin levels less than 10 µg/L, or transferrin iron saturation levels less than 20%. In other particular embodiments, an individual being treated may have an iron deficiency characterized by ferritin levels less than 100 µg/L.

Treatment Dose of Iron

One having ordinary skill in the art would recognize that embodiments of the methods of the present invention, contemplate, in part, to transdermally deliver a therapeutically effective amount of iron to treat an individual in need thereof, including transdermal iontophoretic delivery, whereas previous methods of transdermal iron administration have administered sub-therapeutic doses of iron. For example, the average adult male has about 3-4 grams of iron in his body, the adult female, about 2-3 grams. During daily metabolism, adult males lose about 1-2 mg of iron per day, while adult females lose about 3-4 mg of iron per day (depending on whether the female is pregnant, pre- or post-menopausal). During illness, adult males and females can lose up to 5-6 mg of iron daily. Previous transdermal delivery methods have delivered a daily dose of no more than 0.7 mg/day. The skilled artisan would recognize that this sub-therapeutic dose is not even sufficient for the maintenance of normal physiological iron levels, given that the daily turnover of iron is more than twice that amount.

In contrast, embodiments of the methods of the present invention provide for the transdermal delivery of a therapeutic dose of iron. Accordingly, various embodiments of the invention provide a patch for the transdermal delivery of a composition comprising one or more iron-containing compounds which comprise a therapeutically effective amount of iron. Embodiments of the patch can include a transdermal iontophoretic patch including one or more ionic iron containing compounds comprising the therapeutically effective amount of iron. The therapeutically effective amount of iron can include a variety of ranges. In particular embodiments, the therapeutically effective amount of iron contained in the patch can be in a range of about 10 mg to about 10 grams of elemental iron, in a range of about 10 mg to about 5 grams of elemental iron, in a range of about 10 mg to about 1 gram of elemental iron, in a range of about 10 mg to about 900 mg of elemental iron, in a range of about 10 mg to about 800 mg of elemental iron, in a range of about 10 mg to about 700 mg of elemental iron, in a range of about 10 mg to about 600 mg of elemental iron, in a range of about 10 mg to about 500 mg of elemental iron, in a range of about 10 mg to about 400 mg of elemental iron, in a range of about 10 mg to about 300 mg of elemental iron, in a range of about 10 mg to about 200 mg of elemental iron, in a range of about 10 mg to about 100 mg of elemental iron, in a range of about 10 mg to about 50 mg of elemental iron, or in a range of about 10 mg to about 25 mg of elemental iron, or any intervening range of elemental iron.

In specific embodiments, the iron-containing compound contained in the patch comprises a therapeutically effective amount of about 10 mg of elemental iron, about 25 mg of elemental iron, about 50 mg of elemental iron, about 100 mg of elemental iron, about 200 mg of elemental iron, about 300 mg of elemental iron, about 400 mg of elemental iron, about 500 mg of elemental iron, about 600 mg of elemental iron, about 700 mg of elemental iron, about 800 mg of elemental iron, about 900 mg of elemental iron, about 1 g of elemental iron, about 5 g of elemental iron, about 10 mg of elemental iron, or any intervening amount of elemental iron. For example, in one embodiment, a patch for the transdermal delivery of iron-containing compound comprises a therapeutically effective amount of about 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, or 25 mg of elemental iron.

One having ordinary skill in the art would appreciate that the foregoing amounts of therapeutically effective amounts of elemental iron may be obtained from different combinations of iron-containing compounds (e.g., ferrous salts) of the present invention as described elsewhere herein.

In other particular embodiments, a patch for the transdermal delivery of a composition comprising at least one iron-containing compound (which can comprise an ionic iron containing compound) can be configured to deliver a therapeutically effective amount of about 10 mg of elemental iron per day, about 15 mg of elemental iron per day, about 20 mg of elemental iron per day, about 25 mg of elemental iron per day, about 30 mg of elemental iron per day, about 35 mg of elemental iron per day, about 40 mg of elemental iron per day, about 50 mg of elemental iron per day, about 100 mg of elemental iron per day, about 200 mg of elemental iron per day, about 300 mg of elemental iron per day, about 400 mg of elemental iron per day, about 500 mg of elemental iron per day, or about 1 g of elemental iron per day or any intervening amount of elemental iron per day.

In other particular embodiments, a patch for the transdermal delivery of a composition comprising at least one iron-containing compound (which can comprise an ionic iron containing compound) can be configured to deliver a therapeutically effective amount of at least 10 mg of elemental iron per day, at least 15 mg of elemental iron per day, at least 20 mg of elemental iron per day, at least 25 mg of elemental iron per day, at least 30 mg of elemental iron per day, at least 35 mg of elemental iron per day, at least 40 mg of elemental iron per day, at least 50 mg of elemental iron per day, at least 100 mg of elemental iron per day, at least 200 mg of elemental iron per day, at least 300 mg of elemental iron per day, at least 400 mg of elemental iron per day, at least 500 mg of elemental iron per day, or at least 1 g of elemental iron per day or any intervening amount of elemental iron per day.

In still other particular embodiments, a patch for the transdermal delivery of a composition comprising one or more iron-containing compound (which can comprise an ionic iron containing compound) can be configured deliver a therapeutically effective amount of about 10 mg to about 1 g of elemental iron per day, about 10 mg of elemental iron per day to about 500 mg of elemental iron per day, about 10 mg of elemental iron per day to about 250 mg of elemental iron per day, about 10 mg of elemental iron per day to about 100 mg of elemental iron per day, about 10 mg of elemental iron per day to about 50 mg of elemental iron per day, about 10 mg of elemental iron per day to about 25 mg of elemental iron per day or any intervening amount of elemental iron per day.

In certain embodiments, wherein the individual being treated is a neonate, infant, or child, a patch for the transdermal delivery of a composition comprising one or more iron-containing compounds (which can comprise an ionic iron containing compound) can comprise a therapeutically effective amount in a range of about 1 mg to about 100 mg of elemental iron, a range of about 1 mg to about 90 mg of elemental iron, a range of about 1 mg to about 80 mg of elemental iron, a range of about 1 mg to about 70 mg of elemental iron, a range of about 1 mg to about 60 mg of elemental iron, a range of about 1 mg to about 50 mg of elemental iron, a range of about 1 mg to about 40 mg of elemental iron, a range of about 1 mg to about 30 mg of elemental iron, about 1 mg to about 20 mg of elemental iron, a range of about 1 mg to about 10 mg of elemental iron, or any intervening range of elemental iron. The amount of delivered iron can be adjusted based on one or more of the child's age, weight (e.g., 2 mg/day per kg body weight), size or other anthropomorphic parameter (as well as ferritin level, or transferrin iron saturation level or other indicator of iron deficiency.

In still other certain embodiments, wherein the individual being treated is a neonate, infant, or child, a patch for the transdermal delivery of a composition comprising at least one iron-containing compound (which can comprise an ionic iron containing compound) comprises a therapeutically effective amount of about 1 mg of elemental iron, about 10 mg of elemental iron, about 20 mg of elemental iron, about 30 mg of elemental iron, about 40 mg of elemental iron, about 50 mg of elemental iron, about 60 mg of elemental iron, about 70 mg of elemental iron, about 80 mg of elemental iron, about 90 mg of elemental iron, about 100 mg of elemental iron or any intervening range of elemental iron.

In certain particular embodiments, wherein the individual being treated is a neonate, infant, or child, a patch for the transdermal delivery of a composition comprising at least one iron-containing compound (which can comprise an ionic iron containing compound) delivers a therapeutically effective amount of about 0.5 mg of elemental iron per day, about 1 mg of elemental iron per day, about 2 mg of elemental iron per day, about 5 mg of elemental iron per day, about 10 mg of elemental iron per day, about 15 mg of elemental iron per day, about 20 mg of elemental iron per day, about 25 mg of elemental iron per day, about 30 mg of elemental iron per day, about 35 mg of elemental iron per day, about 45 mg of elemental iron per day, about 50 mg of elemental iron per day, about 75 mg of elemental iron per day, or about 100 mg of elemental iron per day or any intervening amount of elemental iron per day.

In a particular embodiment, a pharmaceutical composition comprising a therapeutically effective amount of iron is continuously delivered for a period of about 1 day, about 2 days, about 3 days, about 4 days, about 5 days, about 6 days, about 1 week, about 2 weeks, about 3 weeks, about 1 month, about 2 months, or longer or any intervening period of time.

In another particular embodiment, a pharmaceutical composition comprising a therapeutically effective amount of iron is continuously delivered for a period of about 1 day to about 2 months, about 1 day to about 1 month, about 1 day to about 1 week, about 1 day to about 5 days, about 1 day to about 3 days or about 1 to 2 days or any intervening period of time.

Thus, in an embodiment, a method for treating and/or preventing an iron deficiency in an individual comprises: i) contacting the individual with a transdermal patch of the present invention, which comprises a pharmaceutical composition comprising a therapeutically effective amount of iron from at least one iron-containing compound as described herein (which can comprise an ionic iron containing compound); ii) delivering a therapeutically effective amount of elemental iron to the individual, thereby preventing and/or treating an iron deficiency in an individual.

In another embodiment, the pharmaceutical compositions of the present invention comprise a therapeutically effective amount of iron from one or more iron-containing compounds (which can comprise an ionic iron containing compound), and/or one or more compounds or agents selected from the group consisting of vitamin supplements, erythropoietin stimulating agents, erythropoietin, pharmaceutically acceptable carriers, transdermal permeabilizing agents, and cyclodextrins as described elsewhere throughout herein.

The present invention contemplates, in part, that in particular embodiments, a method for treating and/or preventing an iron deficiency in an individual comprises: i) contacting the individual with a transdermal patch of the Present invention, which comprises a pharmaceutical composition comprising a therapeutically effective amount of iron from at least one iron-containing compound as described herein (which can comprise an ionic iron containing compound); ii) delivering a therapeutically effective amount of elemental iron to the individual, and further comprises parenteral (e.g., injection via an intravascular, intravenous, intramuscular, subcutaneous or intramuscular route) or oral administration of a therapeutically effective dose of iron.

One having ordinary skill in the art is experienced in practicing parenteral and oral administrations of iron as explained above, and thus, can readily prepare and administer these iron formulations without further guidance herein.

In a particular embodiment, the parenteral or oral iron administration is achieved before, at the same time or after contacting the individual with a transdermal patch of the present invention comprising a therapeutically effective dose of elemental iron. Without wishing to be bound by any particular theory, the present invention contemplates, in part, that a therapeutically effective dose of iron administered via an oral or parenteral route will rapidly act to increase the physiological iron levels of an individual suffering from an iron deficiency back to within the normal limits of physiological iron levels. Normal iron levels in these patients could then be maintained by the continuous transdermal delivery of iron as described throughout herein.

The amount of parenterally or orally administered iron can be about 100 mg of elemental iron, about 200 mg of elemental iron, about 300 mg of elemental iron, about 400 mg of elemental iron, about 500 mg of elemental iron, about 600 mg of elemental iron, about 700 mg of elemental iron, about 800 mg of elemental iron, about 900 mg of elemental iron, about 1 g of elemental iron, or any intervening amount of iron.

In a particular embodiment, the amount of parenterally or orally administered iron can be in a range of about 100 mg of elemental iron to about 1 gram of elemental iron, in a range of about 200 mg of elemental iron to about 1 gram of elemental iron, in a range of about 300 mg of elemental iron to about 1 gram of elemental iron, in a range of about 400 mg of elemental iron to about 1 gram of elemental iron, in a range of about 500 mg of elemental iron to about 1 gram of elemental iron, in a range of about 600 mg of elemental iron to about 1 gram of elemental iron, in a range of about 700 mg of elemental iron to about 1 gram of elemental iron, in a range of about 800 mg of elemental iron to about 1 gram of elemental iron, in a range of about 900 mg of elemental iron to about 1 gram of elemental iron, or any intervening amount of iron.

Thus, in one embodiment, a method for treating and/or preventing an iron deficiency in an individual comprises: i) contacting the individual with a transdermal patch of the present invention, which comprises a pharmaceutical composition comprising a therapeutically effective amount of iron from at least one iron-containing compound as described herein (which can comprise an ionic iron containing compound); ii) delivering a therapeutically effective amount of iron to the individual, optionally administering a parenteral or oral dose of a therapeutically effective amount of iron, thereby preventing and/or treating an iron deficiency in an individual.

One having ordinary skill in the art would be able to practice any of the embodiments described herein. Moreover, one of skill in the art could combine various embodiments described herein to provide further embodiments.

All of the U.S. patents, U.S. patent application publications, U.S. patent applications, foreign patents, foreign patent applications and non-patent publications referred to in this specification and/or listed in the Application Data are incorporated herein by reference, in their entirety.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example embodiments of the apparatus can be sized and otherwise adapted for various pediatric and neonatal applications.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for the transdermal iontophoretic delivery of a composition comprising ionic iron to an individual in need thereof, comprising:
    contacting the individual with a patch comprising an active electrode and a reservoir including a composition comprising ionic iron, the reservoir and composition being separate from the electrode; and
    applying current from the active electrode to the reservoir to cause transdermal iontophoretic delivery of a therapeutically effective amount of ionic iron from the reservoir to the individual, wherein the composition does not include heme iron or heme iron polypeptide.

2. The method of claim 1, wherein the ionic iron is in the form of one or more ferrous salts.

3. The method of claim 2, wherein the one or more ferrous salts are selected from the group consisting of: ferrous gluconate, ferrous chloride, ferrous sulfate, and ferrous fumarate.

4. The method of claim 1, wherein the composition comprises at least one agent selected from the group consisting of: a vitamin supplement, erythropoietin, and an erythropoietin stimulating agent.

5. The method of claim 4, wherein the vitamin supplement is selected from the group consisting of thiamine, riboflavin, niacin, pantothenic acid, pyroxidine, biotin, folic acid, and cobalamin.

6. The method of claim 1, wherein the therapeutically effective amount of delivered ionic iron is in a range from about 1 mg to about 50 mg of elemental iron.

7. The method of claim 1, wherein the therapeutically effective amount of delivered ionic iron is in a range from about 1 mg to about 40 mg of elemental iron.

8. The method of claim 1, wherein the therapeutically effective amount of delivered ionic iron is in a range from about 1 mg to about 30 mg of elemental iron.

9. The method of claim 1, further comprising adjusting the therapeutically effective amount of ionic delivered iron to the individual based on a treatment parameter.

10. The method of claim 9, wherein the treatment parameter is a patient characteristic, patient weight, type of iron deficiency being treated or selected therapeutic outcome.

11. The method of claim 1, wherein the ionic iron composition is delivered substantially continuously.

12. The method of claim 1, wherein the ionic iron composition is delivered over a period of about one day to about one month.

13. The method of claim 1, wherein the ionic iron composition is delivered over a period of about one day to about one week.

14. The method of claim 13, wherein the ionic iron composition is delivered over a period of about one day to about three days.

15. The method of claim 14, wherein the ionic iron composition is delivered over a period of about one day.

16. The method of claim 15, wherein the therapeutically effective amount of delivered ionic iron is in a range from about 1 mg to about 50 mg of elemental iron.

17. The method of claim 1, further comprising: delivering sufficient iron to prevent and/or treat an iron deficiency in an individual.

18. The method of claim 17, further comprising administering a parental therapeutically effective amount of iron.

19. The method of claim 18, wherein the parental administration is done prior to transdermal delivery.

20. The method of claim 18, wherein the parental administration is intravenous or subcutaneous.

21. The method of claim 18, wherein at least one of the parental administration and the transdermal delivery are adjusted relative to the other.

22. The method of claim 21, wherein the adjustment is in at least one of a rate or amount of iron delivery.

23. The method of claim 17, further comprising administering an oral therapeutically effective amount of iron.

24. The method of claim 23, wherein the oral administration is done prior to the transdermal delivery.

25. The method of claim 17, further comprising administering an intravenous bolus of iron to the individual prior transdermal delivery wherein the bolus contains about 500 mg to 1 gram of iron.

26. The method of claim 17, wherein the individual has an iron deficiency without anemia.

27. The method of claim 26, wherein the iron deficiency is being treated in order to prevent growth retardation, cognitive disabilities, and/or mental retardation.

28. The method of claim 26, wherein the iron deficiency, is caused by chronic alcoholism; poor nutrition; decreased consumption of animal protein and absorbic acid; increased iron demands of pregnancy, infancy, or adolescence; malabsorption syndromes; and foods or drugs that reduce the gastrointestinal absorption of iron.

29. The method of claim 17, wherein the individual has an iron deficiency anemia.

30. The method of claim 29, wherein the individual has an iron deficiency characterized by microcytosis of red blood cells, a hemoglobin iron binding capacity of less than 20%, ferritin levels less than about 10 μg/L, or transferrin iron saturation levels less than 20%.

31. The method of claim 17, wherein the individual has a functional iron deficiency with ferritin levels less than 100 μg/L.

32. The method of claim 17, wherein the individual is selected from the group consisting of a child, infant, and neonate.

33. The method of claim 17, wherein the therapeutically effective amount of delivered ionic iron is in a range from about 0.5 mg to about 40 mg of elemental iron.

34. The method of claim 17, wherein the therapeutically effective amount of delivered ionic iron is in a range from about 0.5 mg to about 20 mg of elemental iron.

35. The method of claim 17, wherein the therapeutically effective amount of delivered ionic iron is adjusted based on an anthropomorphic parameter or an indicator of iron deficiency.

36. The method of claim 17, wherein the ionic iron composition is delivered over a period of about one day to about one week.

37. The method of claim 1, further comprising: creating a plurality of micro channels in the stratum corneum to enhance transdermal delivery of the ionic iron.

38. The method of claim 37, wherein the plurality of microchannels are created mechanically.

39. The method of claim 38, wherein the plurality of microchannels are created using a plurality of needles.

40. The method of claim 38, wherein the plurality of microchannels are created using an electrical discharge on or into the skin.

41. The method of claim 40, wherein the discharge is created using a plurality of conductive microfilaments.

42. A method for the transdermal iontophoretic delivery of a composition comprising ionic iron to an individual in need thereof, the method comprising:

contacting the individual with a patch comprising an active electrode and a reservoir including a pharmaceutical composition comprising ionic iron, wherein the composition is uniformly distributed within the reservoir, the reservoir and composition being separate from the electrode; and applying current from the active electrode to the reservoir to cause transdermal iontophoretic delivery of a therapeutically effective amount of ionic iron from the reservoir to the individual wherein the composition does not include heme iron or heme iron polypeptide.

* * * * *

UNITED STATES PATENT AND TRADEMARK OFFICE
CERTIFICATE OF CORRECTION

| | | |
|---|---|---|
| PATENT NO. | : 8,996,104 B2 | Page 1 of 1 |
| APPLICATION NO. | : 12/459183 | |
| DATED | : March 31, 2015 | |
| INVENTOR(S) | : Ronald J. Berenson | |

It is certified that error appears in the above-identified patent and that said Letters Patent is hereby corrected as shown below:

In the Claims,

Claim 18

Column 31, line 67, delete "parental" and replace with --parenteral--.

Claim 19

Column 32, line 1, delete "parental" and replace with --parenteral--.

Claim 20

Column 32, line 3, delete "parental" and replace with --parenteral--.

Claim 21

Column 32, line 6, delete "parental" and replace with --parenteral--.

Signed and Sealed this
Twenty-ninth Day of December, 2015

Michelle K. Lee
*Director of the United States Patent and Trademark Office*